United States Patent
Su

(10) Patent No.: US 11,890,479 B2
(45) Date of Patent: *Feb. 6, 2024

(54) SELECTION OF PARAMETERS FOR ELECTRICAL STIMULATION

(71) Applicant: Medtronic, Inc., Minneapolis, MN (US)

(72) Inventor: Xin Su, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 38 days.

This patent is subject to a terminal disclaimer.

(21) Appl. No.: 17/653,670

(22) Filed: Mar. 7, 2022

(65) Prior Publication Data
US 2022/0257943 A1     Aug. 18, 2022

Related U.S. Application Data

(63) Continuation of application No. 16/215,072, filed on Dec. 10, 2018, now Pat. No. 11,273,311.

(51) Int. Cl.
| | |
|---|---|
| *A61N 1/36* | (2006.01) |
| *A61N 1/02* | (2006.01) |
| *A61N 1/372* | (2006.01) |

(52) U.S. Cl.
CPC .......... *A61N 1/3615* (2013.01); *A61N 1/025* (2013.01); *A61N 1/36175* (2013.01);
(Continued)

(58) Field of Classification Search
CPC ................ A61N 1/025; A61N 1/36031; A61N 1/36062; A61N 1/36071; A61N 1/36139;
(Continued)

(56) References Cited

U.S. PATENT DOCUMENTS

| | | |
|---|---|---|
| 6,366,813 B1 | 4/2002 | DiLorenzo |
| 7,706,871 B2 | 4/2010 | Devlin et al. |

(Continued)

OTHER PUBLICATIONS

Abejon et al., "Threshold Evolution as an Analysis of the Different Pulse Frequencies in Rechargeable Systems for Spinal Cord Stimulation," Neuromodulation: Technology at the Neural Interface, vol. 19, Dec. 27, 2015, pp. 276-282.

(Continued)

*Primary Examiner* — Jon Eric C Morales
(74) *Attorney, Agent, or Firm* — Shumaker & Sieffert, P.A.

(57) ABSTRACT

Devices, systems, and techniques for controlling electrical stimulation therapy are described. In one example, a system may include processing circuitry configured to control a medical device to deliver a first electrical stimulation according to a first value of a first stimulation parameter of the plurality of stimulation parameters and a first value of a second parameter of the plurality of stimulation parameters, receive an input representative of an efficacy of the first electrical stimulation delivered to the patient according to the first value of the first stimulation parameter and the first value of the second parameter, select, based on the input and the relationship between the plurality of stimulation parameters, a second value of at least one of the first stimulation parameter or the second stimulation parameter, and control the medical device to deliver a second electrical stimulation according to the second value.

20 Claims, 15 Drawing Sheets

(52) U.S. Cl.
CPC ..... *A61N 1/36192* (2013.01); *A61N 1/36196* (2013.01); *A61N 1/37247* (2013.01)

(58) Field of Classification Search
CPC .............. A61N 1/3615; A61N 1/36175; A61N 1/36192; A61N 1/36196; A61N 1/37247
See application file for complete search history.

(56) References Cited

U.S. PATENT DOCUMENTS

| | | | |
|---|---|---|---|
| 7,983,757 | B2 | 7/2011 | Miyazawa et al. |
| 8,918,177 | B2 | 12/2014 | Gauthier |
| 9,295,840 | B1 | 3/2016 | Thacker et al. |
| 9,352,161 | B2 | 5/2016 | Thacker et al. |
| 9,517,344 | B1 | 12/2016 | Bradley |
| 10,183,168 | B2 | 1/2019 | Baru et al. |
| 11,273,311 | B2 | 3/2022 | Su |
| 2010/0274320 | A1 | 10/2010 | Torgerson |
| 2014/0236257 | A1 | 8/2014 | Parker et al. |
| 2014/0243926 | A1 | 8/2014 | Carcieri |
| 2018/0133484 | A1 | 5/2018 | Dinsmoor et al. |

OTHER PUBLICATIONS

De Ridder et al., "Burst Spinal Cord Stimulation: Toward Paresthesia-Free Pain Suppression," Neurosurgery, vol. 66, No. 5, May 2010, pp. 986-990.

Extended European Search Report from counterpart European Application No. 19207509.1, dated May 7, 2020, 7 pp.

Miller et al., "Parameters of Spinal Cord Stimulation and Their Role in Electrical Charge Delivery: a Review," Neuromodulation, Feb. 15, 2016, vol. 19, 373-384.

Prosecution History from U.S. Appl. No. 16/215,072, now issued U.S. Pat. No. 11,273,311, dated Feb. 16, 2021 through Nov. 3, 2021, 57 pp.

SELECTION OF PARAMETERS FOR ELECTRICAL STIMULATION

This application is a continuation of U.S. patent application Ser. No. 16/215,072, filed Dec. 10, 2018, the entire contents of which is incorporated herein by reference.

TECHNICAL FIELD

This disclosure generally relates to electrical stimulation, and more specifically, selection of parameters defining electrical stimulation therapy.

BACKGROUND

Medical devices may be external or implanted and may be used to deliver electrical stimulation to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively. Electrical stimulation may be delivered by the medical device as a train of pulses, and the values of the parameters defining the pulses may be altered.

SUMMARY

Systems, devices, and techniques are described for selecting values of stimulation parameters that at least partially define electrical stimulation for a patient. The values selected for one or more stimulation parameters may be based on one or more stimulation parameter values used to define electrical stimulation already delivered to the patient, and in some examples, a pre-defined relationship between two or more stimulation parameters. For example, a system may select a new value for a first stimulation parameter based on a stored relationship between the first stimulation parameter and a second stimulation parameter. In another example, the system may shift between different zones of stimulation intensity as needed to deliver effective therapy, where each zone is defined by a different combination of pulse amplitude, pulse width, and/or pulse frequency. In another example, a target stimulation intensity may be determined from a value of an evoked compound action potential (ECAP) at a first set of stimulation parameter values. The system may then deliver stimulation using a second set of stimulation parameter values based on a relationship between two or more stimulation parameters of the first set and the second set where the ECAP is not detectable using the second set of stimulation parameter values.

In one example, a system includes: a memory configured to store a relationship between a plurality of stimulation parameters, wherein values of the plurality of stimulation parameters are selectable to at least partially define electrical stimulation deliverable to a patient; and processing circuitry configured to control a medical device to deliver a first electrical stimulation according to a first value of a first stimulation parameter of the plurality of stimulation parameters and a first value of a second parameter of the plurality of stimulation parameters, receive an input representative of an efficacy of the first electrical stimulation delivered to the patient according to the first value of the first stimulation parameter and the first value of the second parameter, select, based on the input and the relationship between the plurality of stimulation parameters, a second value of at least one of the first stimulation parameter or the second stimulation parameter, and control the medical device to deliver a second electrical stimulation according to the second value of the at least one of the first stimulation parameter or the second stimulation parameter.

In another example, a method includes storing, in memory, a relationship between a plurality of stimulation parameters, wherein values of the plurality of stimulation parameters are selectable to at least partially define electrical stimulation deliverable to a patient, controlling, by processing circuitry, a medical device to deliver a first electrical stimulation according to a first value of a first stimulation parameter of the plurality of stimulation parameters and a first value of a second parameter of the plurality of stimulation parameters, receiving, by the processing circuitry, an input representative of an efficacy of the first electrical stimulation delivered to the patient according to the first value of the first stimulation parameter and the first value of the second parameter, selecting, by the processing circuitry and based on the input and the relationship between the plurality of stimulation parameters, a second value of at least one of the first stimulation parameter or the second stimulation parameter, and controlling, by the processing circuitry, the medical device to deliver a second electrical stimulation according to the second value of the at least one of the first stimulation parameter or the second stimulation parameter.

In another example, a computer-readable storage medium includes instructions that, when executed by processing circuitry of a medical device, cause the processing circuitry to receive a relationship between a plurality of stimulation parameters, wherein values of the plurality of stimulation parameters are selectable to at least partially define electrical stimulation deliverable to a patient, control a medical device to deliver a first electrical stimulation according to a first value of a first stimulation parameter of the plurality of stimulation parameters and a first value of a second parameter of the plurality of stimulation parameters, receive an input representative of an efficacy of the first electrical stimulation delivered to the patient according to the first value of the first stimulation parameter and the first value of the second parameter, select, based on the input and a relationship between the plurality of stimulation parameters, a second value of at least one of the first stimulation parameter or the second stimulation parameter, and control the medical device to deliver a second electrical stimulation according to the second value of the at least one of the first stimulation parameter or the second stimulation parameter.

In another example, a system includes a memory configured to store a relationship between a plurality of stimulation parameters, the plurality of stimulation parameters comprising a pulse frequency and a pulse width, and processing circuitry configured to receive a signal representative of an evoked compound action potential (ECAP) elicited from electrical stimulation, determine, from the signal, a value of the ECAP indicative of a target stimulation intensity at least partially caused by a first set of stimulation parameter values comprising a first value of the pulse frequency and a first value of the pulse width of the electrical stimulation, determine, based on the relationship and the value of the ECAP, a second set of stimulation parameter values comprising at least one of a second value of the pulse frequency greater than the first value of the pulse frequency or a second value of the pulse width greater than the first value of the pulse width, and control a medical device to deliver electrical stimulation according to the second set of stimulation parameter values.

In another example, a method includes storing a relationship between a plurality of stimulation parameters, the plurality of stimulation parameters comprising a pulse frequency and a pulse width, receiving a signal representative of an evoked compound action potential (ECAP) elicited from electrical stimulation, determining, from the signal, a value of the ECAP indicative of a target stimulation intensity at least partially caused by a first set of stimulation parameter values comprising a first value of the pulse frequency and a first value of the pulse width of the electrical stimulation, determining, based on the relationship and the value of the ECAP, a second set of stimulation parameter values comprising at least one of a second value of the pulse frequency greater than the first value of the pulse frequency or a second value of the pulse width greater than the first value of the pulse width, and controlling a medical device to deliver electrical stimulation according to the second set of stimulation parameter values.

In another example, a system includes a memory configured to store a relationship between a plurality of stimulation parameters, wherein values of the plurality of stimulation parameters are selectable to at least partially define electrical stimulation deliverable to a patient, and processing circuitry configured to control a medical device to deliver a first electrical stimulation within a first zone of a plurality of intensity zones to a patient, wherein the first zone comprises a first pulse frequency range and a first pulse width range, determine that the first electrical stimulation provides ineffective therapy for the patient, select, based on the first electrical stimulation providing ineffective therapy for the patient, a second pulse frequency value from a second pulse frequency range of a second zone of the plurality of intensity zones and a second pulse width value from a second pulse width range of the second zone, wherein at least one of the second pulse frequency range is greater than the first pulse frequency range or the second pulse width range is greater than the first pulse width range, and wherein stimulation parameter values selected from the second zone define a second electrical stimulation having a second stimulation intensity greater than a first stimulation intensity of the first electrical stimulation, and control the medical device to deliver the second electrical stimulation to the patient.

In another example, a method includes storing a relationship between a plurality of stimulation parameters, wherein values of the plurality of stimulation parameters are selectable to at least partially define electrical stimulation deliverable to a patient, controlling, by processing circuitry, delivery of a first electrical stimulation within a first zone of a plurality of intensity zones to a patient, wherein the first zone comprises a first pulse frequency range and a first pulse width range, determining, by the processing circuitry, that the first electrical stimulation provides ineffective therapy for the patient, responsive to determining that the first electrical stimulation provides ineffective therapy for the patient, selecting, by the processing circuitry, a second pulse frequency value from a second pulse frequency range of a second zone of the plurality of intensity zones and a second pulse width value from a second pulse width range of the second zone, wherein at least one of the second pulse frequency range is greater than the first pulse frequency range or the second pulse width range is greater than the first pulse width range, and wherein stimulation parameter values selected from the second zone define a second electrical stimulation having a second stimulation intensity greater than a first stimulation intensity of the first electrical stimulation, and controlling, by the processing circuitry, delivery of the second electrical stimulation to the patient.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
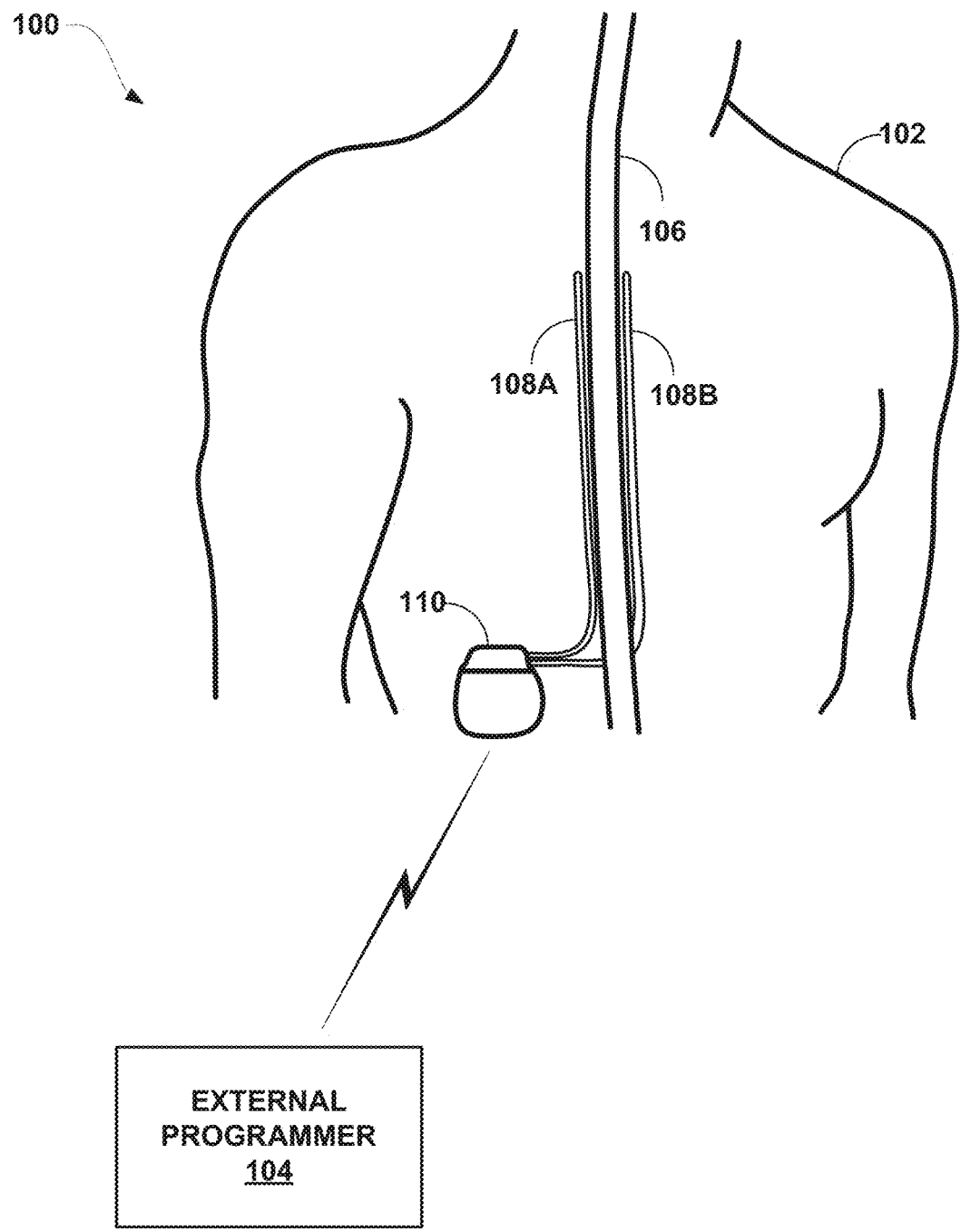
FIG. 1 is a conceptual diagram illustrating an example system that includes a medical device programmer and an implantable medical device (IMD) configured to deliver SCS therapy according to the techniques of the disclosure.

In general, the disclosure describes systems, devices, and techniques for selecting values of one or more stimulation parameters that define electrical stimulation therapy. Electrical stimulation therapy, such as SCS and other types of electrical stimulation therapy, has been used to treat chronic neuropathic pain, organ dysfunction, and other conditions. Electrical stimulation therapy is defined by a set of stimulation parameter values, such as values for pulse amplitude (current and/or voltage), pulse frequency, pulse width, pulse shape, and/or electrode combination. The values for each of these stimulation parameters may be determined via a trial and error process. For example, a physician may manually adjust the pulse amplitude, pulse frequency, and/or pulse width until the patient begins to perceive a therapeutic benefit from the stimulation. A number of stimulation programs defined by different values of stimulation parameters may be programmed for trial by the patient, such that the patient can switch between these different programs over time in an attempt to identify programs that provide effective therapy.

However, this process can be time consuming due to the millions of different stimulation parameter combinations that are possible for the system. Moreover, an adjustment to a value of one stimulation parameter (e.g., pulse width) may change the effectiveness of another stimulation parameter (e.g., pulse frequency). Therefore, in an attempt to manually adjust one stimulation parameter to increase stimulation efficacy, the resulting stimulation efficacy may not be expected because of an unknown contribution from another stimulation parameter that was not changed. Another potential issue with manual parameter value selection is the impact to battery longevity of an IMD. Although an effective set of stimulation parameter values may be found during manual parameter value selection, that set of stimulation parameter values may consume more energy (or be less energy efficient) than a different set of stimulation parameter values that may still provide effective therapy. For example, high-frequency SCS that includes pulses delivered at 10 kHz can be used to achieve sustained effectiveness in the treatment of chronic back pain, but more energy efficiency stimulation at low-frequency 50 Hz-60 Hz pulse frequency may still provide effective therapy for some patients. Moreover, a sensed physiological characteristic, such as an evoked compound action potential (ECAP), may be used to provide closed-loop feedback control of stimulation parameter values. However, ECAPs may not be detectable at all ranges of parameter values, such as during pulses with long pulse widths and/or high frequencies.

As described herein, systems, devices, and techniques provide solutions to one or more of the above-referenced problems with stimulation parameter selection. For example, in one example, the relationship between two stimulation parameters, such as pulse width and pulse frequency, can be used to adjust, or calibrate, the parameter values used to define electrical stimulation. Perhaps a physician desires to change a parameter value increase the electrical charge delivered to the patient in an attempt to increase therapy efficacy. The system may also select, based on the relationship between the parameters, a different value for another stimulation parameter in order to maintain therapy under the strength duration curve (i.e., a curve that defines values of two parameters, such as amplitude and pulse width, that provides a perception threshold below which the patient does not perceive stimulation sensation). The strength duration curve may also be set to define a motor threshold or an uncomfortable threshold. In this manner, the system may be configured to deliver larger amounts of charge to the spinal cord while maintaining sub-perception threshold stimulation, for example. The system may thus utilize an algorithm for automatic SCS dosing. In one example, the known relationship between the two parameters can be used by the system to identify the value of one or more parameters at a second point based on the values the parameters at a first point. For example, if the intensity of the stimulation is known at a pulse width of 0.03 ms, the system can estimate the intensity of the stimulation at a pulse width of 0.3 ms. Or, if the intensity of the stimulation is known at a pulse frequency of 10 Hz, the system can estimate the intensity of the stimulation at a pulse frequency of 1 kHz pulse.

In another example, a system may deliver electrical stimulation according to various zones of charge intensity for SCS. For example, the system may use three different intensity zones that vary electrical charge provided by the stimulation and automatically switch between these zones. Each zone may be defined by a set of stimulation parameters, and each zone is different by at least the value of one stimulation parameter. During a clinic visit, the system may first implement a low energy therapy (e.g., zone 1) to test for efficacy without consuming a large amount of energy. If electrical stimulation is ineffective at zone 1, the system can change stimulation parameters values to zone 2 in an attempt to deliver stimulation therapy that has an increased efficacy. If stimulation according to zone 2 is also not sufficiently effective (e.g., according to patient feedback), the system may again change one or more stimulation parameter values to zone 3. In some examples, each successive zone may consume more energy, so the system may deliver stimulation according to the lower energy zones first in an attempt to find effective therapy at lower energy consumption of an IMD. The pulse intensity for each zone will be estimated based on pre-defined parameter relationships so that the system can automatically switch to different zones and appropriate adjust each stimulation parameter value without clinician intervention.

In another example, the system may determine a target stimulation intensity from ECAPs measured during stimulation defined by a first set of stimulation parameter values. For example, the first set of stimulation parameter values may be a relatively low pulse frequency and low pulse width at which the stimulation pulses do not interfere with sensing of the ECAPs. Then, the system may, using a pre-defined relationship between one or more stimulation parameters and stimulation intensity, determine one or more stimulation parameter values at which the ECAP may be directly measured. For example, if high frequency stimulation (e.g., 1 kHz to 10 kHz) is desired the system may use the pre-defined relationship between the stimulation parameters to select a pulse width and/or stimulation amplitude at the high pulse frequency that may provide a similar stimulation intensity to the ECAP detected at the lower pulse frequency. The intensity may be an amplitude or a charge density. In this manner, the system may be configured to estimate what other combinations of parameter values may result in a similar ECAP amplitude (or stimulation intensity) when the ECAP is not or cannot be directly measured.

The techniques described herein may enable management of chronic pain based on an impact of electrical charge delivered to the nervous system. Some parameters of the SCS include pulse frequency, pulse width, pulse amplitude, intra-pulse interval, duty cycle, and/or waveform shape. Since multiple parameter values may be adjusted to achieve similar stimulation intensities or ECAP amplitudes, the system may be able to shift to different stimulation strategies while maintaining or improving efficacy. For example, the system may be able to increase charge density, or charge over time, while maintaining perceived amplitude to increase efficacy of therapy when needed.

Although SCS is described generally herein as one example, systems may leverage these techniques to deliver other stimulation therapies. For example, relationships between stimulation parameters or stimulation zones may be employed to improve efficacy and/or reduce power consumption in pelvic floor stimulation (e.g., sacral neuromodulation (SNM)), deep brain stimulation (DBS), or peripheral nerve stimulation (PNS), as some examples.

FIG. 1 is a conceptual diagram illustrating example system 100 that includes implantable medical device (IMD) 110 configured to deliver electrical stimulation therapy to patient 102. In the example shown in FIG. 1, IMD 110 is configured to deliver SCS therapy according to the techniques of the disclosure. Although the techniques described in this disclosure are generally applicable to a variety of medical devices including external and implantable medical devices, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 108A and 108B, and external programmer 104 shown in conjunction with a patient 102, who is ordinarily a human patient. In the example of FIG. 1, IMD 110 is an implantable electrical stimulator that is configured to generate and deliver an electrical stimulation signal to patient 102 via one or more electrodes of electrodes of leads 108A and/or 108B (collectively, "leads 108"), e.g., for relief of chronic pain or other symptoms. In other examples, IMD 110 may be coupled to a single lead carrying multiple electrodes or more than two leads each carrying multiple electrodes. IMD 110 may be a chronic electrical stimulator that remains implanted within patient 102 for weeks, months, or even years. In other examples, IMD 110 may be a temporary, or trial, stimulator used to screen or evaluate the efficacy of electrical stimulation for chronic therapy. In one example, IMD 110 is implanted within patient 102, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 102. In this example, IMD 110 may be constructed with a biocompatible housing, such as titanium or stainless steel, or a polymeric material such as silicone, polyurethane, or a liquid crystal polymer, and surgically implanted at a site in patient 102 near the pelvis, abdomen, or buttocks. In other examples, IMD 110 may be implanted within other suitable sites within patient 102, which may depend, for example, on the target site within patient 102 for the delivery of an electrical stimulation signal. The outer housing of IMD 110 may be configured to provide a hermetic seal for components, such as a rechargeable or non-rechargeable power source. In addition, in some examples, the outer housing of IMD 110 may be selected from a material that facilitates receiving energy to charge the rechargeable power source.

Electrical stimulation energy, which may be constant current or constant voltage-based pulses, for example, is delivered from IMD 110 to one or more target tissue sites of patient 102 via one or more electrodes (not shown) of implantable leads 108. In the example of FIG. 1, leads 108 carry electrodes that are placed adjacent to the target tissue of spinal cord 106. One or more of the electrodes may be disposed at a distal tip of a lead 108 and/or at other positions at intermediate points along the lead. Leads 108 may be implanted and coupled to IMD 110. The electrodes may transfer electrical stimulation generated by a stimulation generator in IMD 110 to tissue of patient 102. An electrical stimulation generator can encompass a pulse or signal generator, and the electrical stimulation may be in the form of pulses or continuous waveforms. Although leads 108 may each be a single lead, lead 108 may include a lead extension or other segments that may aid in implantation or positioning of lead 108. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 108 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of leads 108 will be described for purposes of illustration.

The deployment of electrodes via leads 108 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead. In other examples, one or more of leads 108 are linear leads having 8 ring electrodes along the axial length of the lead. In another example, the electrodes are segmented rings arranged in a linear fashion along the axial length of the lead and at the periphery of the lead.

The stimulation parameters that can define the electrical stimulation signal by IMD 110 through the electrodes of leads 108 may include information such as duty cycle, charge per stimulation, pulse amplitude, pulse frequency, pulse width, intra-pulse interval, and waveform shape of stimulation delivered by the electrodes. These stimulation parameters can be predetermined parameter values determined prior to delivery of the stimulation. However, in some examples, system 100 may change one or more parameter values automatically based on one or more factors or based on user input.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 102.

In some examples, leads 108 may include one or more sensors configured to allow IMD 110 to monitor one or more parameters of patient 102, such as patient activity, pressure, temperature, or other characteristics. The one or more sensors may be provided in addition to, or in place of, therapy delivery by leads 108.

IMD 110 is configured to deliver electrical stimulation therapy to patient 102 via selected combinations of electrodes carried by one or both of leads 108, alone or in combination with an electrode carried by or defined by an outer housing of IMD 110. The target tissue for the electrical stimulation may be any tissue affected by an electrical stimulation signal. In some examples, the target tissue includes nerves, smooth muscle or skeletal muscle. In the example illustrated by FIG. 1, the target tissue is tissue proximate spinal cord 106, such as within an intrathecal space or epidural space of spinal cord 106, or, in some examples, adjacent nerves that branch off spinal cord 106. Leads 108 may be introduced into spinal cord 106 via any suitable region, such as the thoracic, cervical or lumbar regions. Stimulation of spinal cord 106 may, for example, prevent pain signals from traveling through spinal cord 106 and to the brain of patient 102. Patient 102 may perceive the interruption of pain signals as a reduction in pain and, therefore, efficacious therapy results. In other examples, stimulation of spinal cord 106 may produce paresthesia which may be reduce the perception of pain by patient 102, and thus, provide efficacious therapy results.

IMD 110 generates and delivers electrical stimulation therapy to a target stimulation site within patient 102 via the electrodes of leads 108 to patient 102 according to one or more electrical stimulation parameter settings. Electrical stimulation parameter settings define values for one or more parameters that define an aspect of the therapy delivered by IMD 110 according to therapy parameter settings. For example, electrical stimulation parameter settings can define delivery of stimulation by IMD 110 in the form of pulses with specific values for pulse amplitude, pulse width, waveform shape, intra-pulse interval, duty cycle, charge per second, and pulse rate (e.g., pulse frequency) for electrical stimulation signals delivered by IMD 110 according to an electrical stimulation program.

A user, such as a clinician or patient 102, may interact with a user interface of an external programmer 104 to program IMD 110. Programming of IMD 110 may refer generally to the generation and transfer of commands, programs, or other information to control the operation of IMD 110. In this manner, IMD 110 may receive the transferred commands and programs from programmer 104 to control electrical stimulation signals (e.g., therapy pulses). For example, external programmer 104 may transmit stimulation parameter settings, stimulation parameter relationship data, an input representative of stimulation efficacy, efficacy threshold settings, patient ECAP characteristics, relationship between the ECAP signal and stimulation parameters (e.g., correlation data), user input, or other information to control the operation of IMD 110, e.g., by wireless telemetry or wired connection.

In some cases, external programmer 104 may be characterized as a physician or clinician programmer if it is primarily intended for use by a physician or clinician. In other cases, external programmer 104 may be characterized as a patient programmer if it is primarily intended for use by a patient. A patient programmer may be generally accessible to patient 102 and, in many cases, may be a portable device that may accompany patient 102 throughout the patient's daily routine. For example, a patient programmer may receive input from patient 102 when the patient wishes to terminate or change electrical stimulation therapy. In general, a physician or clinician programmer may support selection and generation of programs by a clinician for use by IMD 110, whereas a patient programmer may support adjustment and selection of such programs by a patient during ordinary use. In other examples, external programmer 104 may include, or be part of, an external charging device that recharges a power source of IMD 110. In this manner, a user may program and charge IMD 110 using one device or multiple devices.

As described herein, information may be transmitted between external programmer 104 and IMD 110. Therefore, IMD 110 and external programmer 104 may communicate via wireless communication using any techniques known in the art. Examples of communication techniques may include, for example, radiofrequency (RF) telemetry and inductive coupling, but other techniques are also contemplated. In some examples, external programmer 104 may include a communication head that may be placed proximate to the patient's body near the IMD 110 implant site to improve the quality or security of communication between IMD 110 and external programmer 104. Communication between external programmer 104 and IMD 110 may occur during power transmission or separate from power transmission.

In some examples, IMD 110, in response to commands from external programmer 104, delivers electrical stimulation signals according to a plurality of stimulation parameter settings to a target tissue site of the spinal cord 106 of patient 102 via electrodes (not depicted) on leads 108. In some examples, IMD 110 may modify stimulation parameter settings as therapy needs of patient 102 evolve over time. For example, the modification of the stimulation parameter settings may cause the adjustment of at least one parameter of the electrical stimulation signal. When patient 102 receives the same electrical stimulation signal for an extended period, the efficacy of the therapy may be reduced. In some cases, parameters of the electrical stimulation signal may be automatically updated.

IMD 110 may be configured to change electrical stimulation by adjusting the values of one or more stimulation parameters over time. For example, IMD 110 may change one or more stimulation parameter in order to find parameter values that provide more effective stimulation therapy and/or reduce the energy consumed by the therapy (e.g., to increase the battery life of IMD 110). In some examples, IMD 110 may store a relationship between two or more stimulation parameters. The relationship may use stimulation amplitude or intensity at various combinations of parameter values. IMD 110 may then use this relationship to select different parameter values that should provide different stimulation intensities or select different combinations of parameter values than may maintain intensity levels but a different electrical charge. In this manner, IMD 110 may select different stimulation parameters according to the relationship that will provide an estimated result for the patient. In some examples, IMD 110 may switch between different zones of intensity using such a relationship. For example, if a first zone is not effective at delivering therapy, IMD 110 may select stimulation parameters from a different zone of intensity that may provide a different level of intensity for the patient. In some examples, the relationships between the parameters may enable IMD 110 to select parameter values that maintain intensity below a strength-duration curve (e.g., a curve indicating a perception threshold, motor threshold, or discomfort threshold). IMD 110 may also use the relationship to select different parameter values to try and stay within a certain zone of intensity.

In this disclosure, efficacy of the electrical stimulation signal may be indicated by one or more characteristics (e.g., an amplitude of or between one or more peaks or an area under the curve of one or more peaks) of an action potential that is evoked by an electrical stimulation signal delivered by IMD 110 (i.e., a characteristic of the ECAP signal). Electrical stimulation signals delivered by leads 108 of IMD 110 may cause neurons within the target tissue to evoke a compound action potential that travels up and down the target tissue, eventually arriving at sensing electrodes of IMD 110. The amount of action potentials (e.g., number of neurons propagating action potential signals) that are evoked may be based on the various parameters of the electrical stimulation signal such as pulse amplitude, pulse width, pulse frequency, intra-pulse interval, waveform shape (e.g., slew rate at the beginning and/or end of the pulse), duty cycle, charge per second, etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters may contribute to an intensity of the electrical stimulation. In addition, a characteristic of the ECAP signal (e.g., an amplitude) may change based on the distance between the stimulation electrodes and the nerves subject to the electrical field produced by the delivered electrical stimulation signal.

In one example, each electrical stimulation signal may have a pulse width greater than approximately 300 µs, such as between approximately 300 µs and approximately 1000 µs (e.g., 1 millisecond). At these pulse widths, IMD 110 may not sufficiently detect an ECAP signal because the electrical stimulation signal is also detected as an artifact that obscures the ECAP signal. If ECAPs are not adequately recorded, then ECAPs arriving at IMD 110 cannot be used to determine the efficacy of stimulation parameter settings, and electrical stimulation signals cannot be altered according to responsive ECAPs. In some examples, pulse widths may be less than approximately 300 µs, which may increase the number of ECAP signals detected. Similarly, high pulse frequencies may interfere with IMD 110 sufficiently detecting ECAP signals. For example, at pulse frequency values (e.g., greater than 1 kHz) that cause IMD 110 to deliver another pulse before an ECAP from the previous pulse can be detected, IMD 110 may not be capable to detecting the ECAP. Parameter values for electrical stimulation signals will be described in further detail herein.

As described herein, some example techniques for adjusting stimulation parameter values for electrical stimulation signals are based on comparing the value of a characteristic of a measured ECAP signal to a target ECAP characteristic value or using stimulation parameter values at a determined target ECAP characteristic to inform adjustment of one or more parameter values to maintain the target ECAP according to known relationships between parameters. For example, during delivery of an electrical stimulation signal, IMD 110, via two or more electrodes interposed on leads 108, senses electrical potentials of tissue of the spinal cord 106 of patient 102 to measure the electrical activity of the tissue. IMD 110 senses ECAPs from the target tissue of patient 102, e.g., with electrodes on one or more leads 108 and associated sensing circuitry. In some examples, IMD 110 receives a signal indicative of the ECAP from one or more sensors, e.g., one or more electrodes and circuitry, internal or external to patient 102. Such an example signal may include a signal indicating an ECAP of the tissue of the patient 102. Examples of the one or more sensors include one or more sensors configured to measure a compound action potential of the patient 102, or a physiological effect indicative of a compound action potential. For example, to measure a physiological effect of a compound action potential, the one or more sensors may be an accelerometer, a pressure sensor, a bending sensor, a sensor configured to detect a posture of patient 102, or a sensor configured to detect a respiratory function of patient 102. However, in other examples, external programmer 104 receives a signal indicating a compound action potential in the target tissue of patient 102 and transmits a notification to IMD 110.

In the example of FIG. 1, IMD 110 described as performing a plurality of processing and computing functions. However, external programmer 104 instead may perform one, several, or all of these functions. In this alternative example, IMD 110 functions to relay sensed signals to external programmer 104 for analysis, and external programmer 104 transmits instructions to IMD 110 to adjust the one or more parameters defining the electrical stimulation signal based on analysis of the sensed signals. For example, IMD 110 may relay the sensed signal indicative of an ECAP to external programmer 104. External programmer 104 may compare the parameter value of the ECAP to the target ECAP characteristic value, and in response to the comparison, external programmer 104 may instruct IMD 110 to adjust one or more parameters that define the electrical stimulation signal.

In the example techniques described herein, the stimulation parameter values, efficacy threshold settings, and the target ECAP characteristic values (e.g., values of the ECAP indicative of target stimulation intensity) may be initially set at the clinic but may be set and/or adjusted at home by patient 102. Once the target ECAP characteristic values are set, the example techniques allow for automatic adjustment of stimulation parameters to maintain consistent volume of neural activation and consistent perception of therapy for the patient when the electrode-to-neuron distance changes. The ability to change the stimulation parameter values may also allow the therapy to have long term efficacy, with the ability to keep the intensity of the stimulation (e.g., as indicated by the ECAP) consistent by comparing the measured ECAP values to the target ECAP characteristic value. IMD 110 may perform these changes without intervention by a physician or patient 102.

In some examples, the system may change the target ECAP characteristic value over a period of time. The system may be programmed to change the target ECAP characteristic in order to adjust the intensity of the electrical stimulation signal to provide varying sensations to the patient (e.g., increase or decrease the volume of neural activation). In one example, a system may be programmed to oscillate a target ECAP characteristic value between a maximum target ECAP characteristic value and a minimum target ECAP characteristic value at a predetermined frequency to provide a sensation to the patient that may be perceived as a wave or other sensation that may provide therapeutic relief for the patient. The maximum target ECAP characteristic value, the minimum target ECAP characteristic value, and the predetermined frequency may be stored in the memory of IMD 110 and may be updated in response to a signal from external programmer 104 (e.g., a user request to change the values stored in the memory of IMD 110). In other examples, the target ECAP characteristic value may be programed to steadily increase or steadily decrease to a baseline target ECAP characteristic value over a period of time. In other examples, external programmer 104 may program the target ECAP characteristic value to automatically change over time according to other predetermined functions or patterns. In other words, the target ECAP characteristic value may be programmed to change incrementally by a predetermined amount or predetermined percentage, the predetermined amount or percentage being selected according to a predetermined function (e.g., sinusoid function, ramp function, exponential function, logarithmic function, or the like). Increments in which the target ECAP characteristic value is changed may be changed for every certain number of pulses or a certain unit of time. Although the system may change the target ECAP characteristic value, received ECAP signals may still be used by the system to adjust one or more parameter values of the electrical stimulation signal in order to meet the target ECAP characteristic value.

In some examples, IMD 110 may not be able to measure ECAPs from stimulation that has certain pulse widths and/or pulse frequencies. For example, longer pulse widths and higher pulse frequencies may result in a delivered stimulation pulse overlapping with an ECAP. Since the ECAP amplitude is typically much lower amplitude than the stimulation pulse, the stimulation pulse can cover up any ECAP characteristic value of the signal. However, IMD 110 may use measured ECAPs at short pulse widths and/or lower pulse frequencies to identify a combination of stimulation parameter values that produce an ECAP characteristic value (e.g., intensity) that is representative of effective therapy. IMD 110 may then select longer pulse widths and/or higher pulse frequencies according to the relationship between the pulse width and pulse frequency that are estimated to produce a similar ECAP characteristic value that resulted in the effective therapy.

Figure 2:
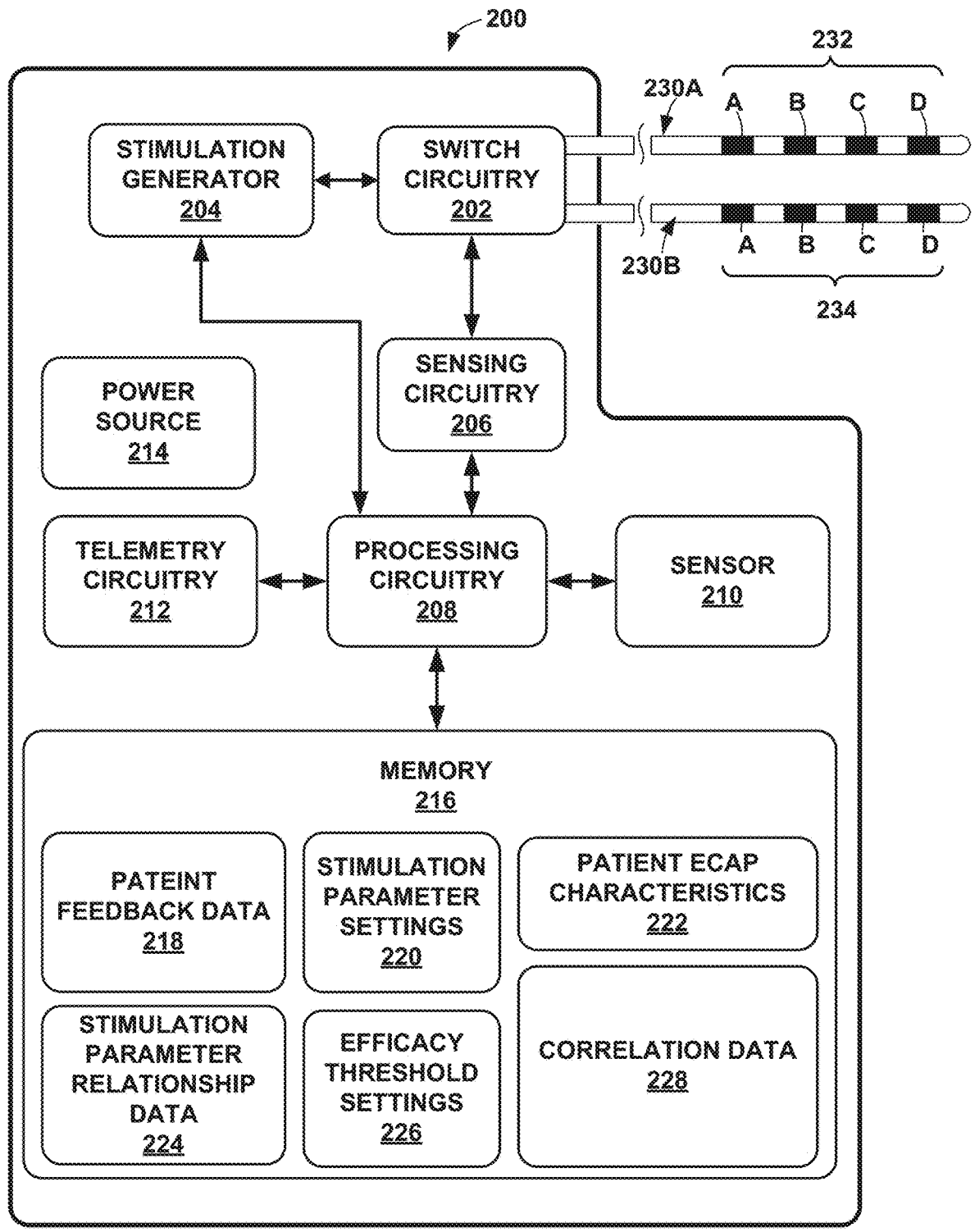
FIG. 2 is a block diagram of the example IMD of FIG. 1.

FIG. 2 is a block diagram of IMD 200. IMD 200 may be an example of IMD 110 of FIG. 1. In the example shown in FIG. 2, IMD 200 includes switch circuitry 202, stimulation generator 204, sensing circuitry 206, processing circuitry 208, sensor 210, telemetry circuitry 212, power source 214, and memory 216. Each of these circuits may be or include programmable or fixed function circuitry configured to perform the functions attributed to respective circuitry. For example, processing circuitry 208 may include fixed-function or programmable circuitry, stimulation generator 204 may include circuitry configured to generate electrical stimulation signals such as pulses or continuous waveforms on one or more channels, sensing circuitry 206 may include sensing circuitry for sensing signals, and telemetry circuitry 212 may include telemetry circuitry for transmission and reception of signals. Memory 216 may store computer-readable instructions that, when executed by processing circuitry 208, cause IMD 200 to perform various functions described herein. Memory 216 may be a storage device or other non-transitory medium.

In the example shown in FIG. 2, memory 216 stores stimulation parameter settings 220 and stimulation parameter relationship data 224 within memory 216 or separate areas within memory 216. Each stored stimulation parameter setting 220 defines values for a set of electrical stimulation parameters (e.g., a therapy parameter set), such as pulse amplitude, pulse width, pulse frequency, electrode combination, pulse burst rate, pulse burst duration, and/or waveform shape. Stimulation parameter settings 220 may also include additional information such as instructions regarding delivery of electrical stimulation signals based on stimulation parameter relationship data 224. Stimulation parameter relationship data 224 may store relationships between two or more stimulation parameters based upon data from electrical stimulation signals delivered to patient 102 or data transmitted from external programmer 104. In some examples, stimulation parameter relationship data 224 may include a relationship between stimulation parameters and a measurable aspect associated with stimulation, such as an ECAP characteristic value or electrogram value.

Memory 216 also stores patient feedback data 218 (e.g., inputs representative of stimulation efficacy) 218 and efficacy threshold settings 226 within memory 216 or separate areas within memory 216. Patient feedback data 218 may include patient input received via programmer 104, for example, that represents the patient's response to the electrical stimulation signals delivered to patient 102. Processing circuitry 208 may use patient feedback data 218 to determine when stimulation therapy is effective and when alternative stimulation parameter values should be identified to improve therapy. Efficacy threshold settings 226 may represent of one or more input, or patient feedback thresholds, that indicate effective or ineffective therapy and may be initially set at the clinic. Additionally, or alternatively, efficacy threshold settings 226 may be set and/or adjusted by a clinician or at home by patient 102 via programmer 104, for example. Efficacy threshold settings 226 may be directed to patient feedback ratings and/or target ECAP characteristics.

Memory 216 may also store patient ECAP characteristics 222 which may include target ECAP characteristics determined for the patient and/or a history of measured ECAP characteristic values for the patient. Memory 216 also stores correlation data 228 (e.g., data indicating a relationship between one or more characteristics of ECAP signals and stimulation parameters) in separate areas from or as part of patient ECAP characteristics 222.

Accordingly, in some examples, stimulation generator 204 generates electrical stimulation signals in accordance with the electrical stimulation parameters. Other ranges of parameter values may also be useful and may depend on the target stimulation site within patient 102. While stimulation signals are described, stimulation signals may be of any form, such as pulses, continuous-time signals (e.g., sine waves) or the like. Stimulation generator 204 can then be described as encompassing a pulse generator or signal generator. Switch circuitry 202 may include one or more switch arrays, one or more multiplexers, one or more switches (e.g., a switch matrix or other collection of switches), or other electrical circuitry configured to direct stimulation signals from stimulation generator 204 to one or more of electrodes 232, 234, or directed sensed signals from one or more of electrodes 232, 234 to sensing circuitry 206. In other examples, stimulation generator 204 and/or sensing circuitry 206 may include sensing circuitry to direct signals to and/or from one or more of electrodes 232, 234, which may or may not also include switch circuitry 202.

Processing circuitry 208 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 208 herein may be embodied as firmware, hardware, software or any combination thereof. Processing circuitry 208 controls stimulation generator 204 to generate electrical stimulation signals according to stimulation parameter settings 220 stored in memory 216 to apply stimulation parameter values, such as pulse amplitude, pulse width, pulse frequency, and waveform shape of each of the electrical stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 208 also controls stimulation generator 204 to generate and apply the electrical stimulation signals to selected combinations of electrodes 232, 234. In some examples, stimulation generator 204 includes a switch circuit (instead of, or in addition to, switch circuitry 202) that may couple stimulation signals to selected conductors within leads 230, which, in turn, deliver the stimulation signals across selected electrodes 232, 234. Such a switch circuit may be a switch array, switch matrix, multiplexer, or any other type of switch circuitry configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generator 204 does not include a switch circuit and switch circuitry 202 does not interface between stimulation generator 204 and electrodes 232, 234. In these examples, stimulation generator 204 comprises a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generator 204, e.g., via switch circuitry 202 and/or switch circuitry of the stimulation generator 204, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generator 204 and processing circuitry 208 in FIG. 2, in other examples, sensing circuitry 206 may be in a separate housing from IMD 200 and may communicate with processing circuitry 208 via wired or wireless communication techniques.

Sensor 210 may include one or more sensing elements that sense values of a respective patient parameter. As described, electrodes 232 and 234 may be the electrodes that sense, via sensing circuitry 206, a value of the ECAP indicative of a target stimulation intensity at least partially caused by a set of stimulation parameter values. Sensor 210 may include one or more accelerometers, optical sensors, chemical sensors, temperature sensors, pressure sensors, or any other types of sensors. Sensor 210 may output patient parameter values that may be used as feedback to control delivery of electrical stimulation signals. IMD 200 may include additional sensors within the housing of IMD 200 and/or coupled via one of leads 108 or other leads. In addition, IMD 200 may receive sensor signals wirelessly from remote sensors via telemetry circuitry 212, for example. In some examples, one or more of these remote sensors may be external to patient (e.g., carried on the external surface of the skin, attached to clothing, or otherwise positioned external to the patient). In some examples, signals from sensor 210 may indicate a position or body state (e.g., sleeping, awake, sitting, standing, or the like), and processing circuitry 208 may select target ECAP characteristic values according to the indicated position or body state.

Telemetry circuitry 212 supports wireless communication between IMD 200 and an external programmer (not shown in FIG. 2) or another computing device under the control of processing circuitry 208. Processing circuitry 208 of IMD 200 may receive, as updates to programs, values for various stimulation parameters such as amplitude and electrode combination, from the external programmer via telemetry circuitry 212. Updates to stimulation parameter settings 220 and input efficacy threshold settings 226 may be stored within memory 216. Telemetry circuitry 212 in IMD 200, as well as telemetry circuits in other devices and systems described herein, such as the external programmer, may accomplish communication by radiofrequency (RF) communication techniques. In addition, telemetry circuitry 212 may communicate with an external medical device programmer (not shown in FIG. 2) via proximal inductive interaction of IMD 200 with the external programmer. The external programmer may be one example of external programmer 104 of FIG. 1. Accordingly, telemetry circuitry 212 may send information to the external programmer on a continuous basis, at periodic intervals, or upon request from IMD 110 or the external programmer.

Power source 214 delivers operating power to various components of IMD 200. Power source 214 may include a rechargeable or non-rechargeable battery and a power generation circuit to produce the operating power. Recharging may be accomplished through proximal inductive interaction between an external charger and an inductive charging coil within IMD 200. In other examples, traditional primary cell batteries may be used. In some examples, processing circuitry 208 may monitor the remaining charge (e.g., voltage) of power source 214 and select stimulation parameter values that may deliver similarly effective therapy at lower power consumption levels when needed to extend the operating time of power source 214. For example, power source 214 may switch to a lower pulse frequency based on the relationships of parameters that may provide similar ECAP characteristic values.

According to the techniques of the disclosure, stimulation generator 204 of IMD 200 receives, via telemetry circuitry 212, instructions to deliver electrical stimulation according to stimulation parameter settings 220 to a target tissue site of the spinal cord of the patient via a plurality of electrode combinations of electrodes 232, 234 of leads 230 and/or a housing of IMD 200. Each electrical stimulation signal may elicit an ECAP that is sensed by sensing circuitry 206 via electrodes 232 and 234. Processing circuitry 208 may receive, via an electrical signal sensed by sensing circuitry 206, information indicative of an ECAP signal (e.g., a numerical value indicating a characteristic of the ECAP in electrical units such as voltage or power) produced in response to the electrical stimulation signal(s). Stimulation parameter settings 220 may be updated according to the ECAPs recorded at sensing circuitry 206 according to the following techniques.

Pulse amplitude (current and/or voltage) for the electrical stimulation signals may be between approximately 0.1 mA (or volts) and approximately 10 mA (or volts), although pulse amplitude may be lower or greater in other examples. In one example, the electrical stimulation signals can each have a pulse width of greater than approximately 10 μs and less than approximately 1000 μs (i.e., 1.0 millisecond). In some examples, the pulse width can be greater than approximately 10 μs and less than approximately 50 μs, greater than approximately 100 μs and less than approximately 500 μs, greater than approximately 10 μs and less than approximately 100 μs, or greater than approximately 100 μs and less than approximately 1000 μs. If relatively long pulse widths of electrical stimulation signals are used, sensing circuitry 206 may be incapable of adequately recording ECAP signals elicited from the electrical simulation signal because the electrical simulation signal may occur during the ECAP signal and obscure the ECAP signal. However, electrical stimulation signals with pulse widths less than approximately 300 μs may be suited to elicit an ECAP which can be sensed after the electrical stimulation signal is completed at sensing circuitry 206 via two or more of electrodes 232 and 234.

In some examples, the pulse frequency of the electrical stimulation signal may be delivered at a frequency that varies over time. In one example, the predetermined pulse frequency of the plurality of electrical stimulation signals may be less than approximately 15 kilohertz (kHz) or greater than approximately 1 Hz. In some examples, the predetermined pulse frequency may be from approximately 1 Hz to approximately 5 kHz, from approximately 1 kHz to approximately 15 kHz, from approximately 1 Hz to approximately 3 kHz, from approximately 3 kHz to approximately 12 kHz, from approximately 5 kHz to approximately 10 kHz, from approximately 10 Hz to approximately 1 kHz. However, the electrical stimulation signals may have frequencies greater than approximately 20 kHz or less than 1 Hz in other examples. As discussed herein, some zones of intensities may include different overlapping or non-overlapping pulse frequencies. For example, a first zone may have a frequency range of about 10 Hz to about 1 kHz, a second zone may have a frequency range of about 10 Hz to about 1 kHz (although the second zone may have a longer pulse width), and a third zone may have a frequency range of about 5 kHz to about 10 kHz. In addition, the electrical stimulation signals may be delivered in bursts of electrical stimulation signals, with interburst frequencies of the electrical stimulation signals being selected such that an ECAP can be sensed within the window between consecutive bursts of electrical stimulation signals.

In some examples, processing circuitry 208 may be configured to change one or more values in stimulation parameter settings 220 as described herein. For example, a parameter value may be changed according to pre-determined relationships between two or more parameters in order to provide alternative charge density and possibly improve efficacy, a parameter value may be changed to move to a different zone of intensity, or a parameter value may be changed based on ECAPs received in response to the electrical stimulation signals delivered to the patient according to the correlation data 228. For instance, processing circuitry 208 may update stimulation parameter settings 220 in real time by comparing one or more characteristic values of ECAPs sensed by sensing circuitry 206 with target ECAP characteristics stored in memory 216 (e.g., patient ECAP characteristics 222). In cases in which ECAP signals cannot be measured due to stimulation pulse interference with the ECAP signal, processing circuitry 208 may be configured to extrapolate the target ECAP value based on the relationship between parameter values and known ECAP values at these other parameter values.

In one example, processing circuitry 208 can store a relationship between the plurality of stimulation parameters in memory 216 in the stimulation parameter relationship data 224. The plurality of stimulation parameters set in the stimulation parameter settings 220 can include at least a pulse frequency and a pulse width. Processing circuitry 208 can receive a signal representative of an ECAP elicited from the electrical stimulation. In some examples, processing circuitry 208 can determine, from the signal, a value of the ECAP indicative of a target stimulation intensity at least partially caused by a first set of stimulation parameter values from the stimulation parameter settings 220 that defines a first value of the pulse frequency and a first value of the pulse width of the electrical stimulation. Processing circuitry 208 can determine, based on the stimulation parameter relationship data 224 and the value of the ECAP, a second set of stimulation parameter values defined by at least one of a second value of the pulse frequency being greater than the first value of the pulse frequency or a second value of the pulse width being greater than the first value of the pulse width. Put another way, processing circuitry 208 can change the pulse frequency to achieve a desired ECAP value or other measure of stimulation intensity and, based on the relationship of the parameters, select a corresponding pulse width to use with the changed pulse frequency. Processing circuitry 208 can instruct stimulation generator 204 to deliver electrical stimulation according to the second set of stimulation parameter values. Stimulation parameter settings 220 can have multiple sets of stimulation parameter values (e.g., multiple stimulation programs), where each set of stimulation parameter values defines a different pulse or set of pulses that can be delivered separately or interleaved with one another over time.

Processing circuitry 208 can determine the second set of stimulation parameter values of the stimulation parameter settings 220 by selecting at least the second value of the pulse frequency or the second value of the pulse width from values under a strength-duration curve representing stimulation parameter relationship data 224. In some examples, stimulation parameter relationship data 224 includes relationships between at least one of amplitude and pulse frequency or amplitude and pulse width indicative of the target stimulation intensity. Determining the second set of stimulation parameter values, as defined by stimulation parameter settings 220, can also include selecting the second value of the pulse frequency to be greater than the first value of the pulse frequency and the second value of the pulse width to be greater than the first value of the pulse width. In other examples, an increase in pulse frequency may result in a selected decrease in pulse width, or vice versa, to achieve similar stimulation intensity because charge delivered may be a function of at least the width of each pulse, amplitude of each pulse, and the amount of pulses in a given period of time. In some examples, determining the relationship between the plurality of stimulation parameters can include determining the relationship between the value of the ECAP indicative of the target stimulation intensity and the plurality of stimulation parameters (e.g., as stored in correlation data 228).

In some examples, memory 216 can store a relationship between a plurality of stimulation parameters (e.g., stimulation parameter relationship data 224). The values of the plurality of stimulation parameters can be selected to at least partially define the electrical stimulation delivered to a patient. Processing circuitry 208 can control stimulation generator 204 to deliver a first electrical stimulation according to a first value of a first stimulation parameter of the plurality of stimulation parameters and a first value of a second parameter of the plurality of stimulation parameters. In some instances, the selections for the stimulation parameter values can be stored in stimulation parameter settings 220. Processing circuitry 208 can receive an input representative of an efficacy of the first electrical stimulation delivered to the patient according to the first value of the first stimulation parameter and the first value of the second parameter. For example, the input may be binary indicating effective or non-effective therapy, or the input may be a rating on a pre-defined scale (e.g., an increasingly effectiveness scale from 1 to 5 or 1 to 10). In some examples, the input may provide a rating on positive attributes of the stimulation and/or undesirable attributes of the stimulation. Based on the input and the relationship between the plurality of stimulation parameters, processing circuitry 208 can select a second value of at least one of the first stimulation parameter or the second stimulation parameter intended to improve the efficacy of the stimulation therapy. In addition, according to the second value of the at least one of the first stimulation parameter or the second stimulation parameter, processing circuitry 208 can control stimulation generator 204 to deliver a second electrical stimulation. In some examples, an external medical device may be used instead of stimulation generator 204, and at least one of IMD 200 or an external programmer (e.g., external programmer 104) in communication with IMD 200 contains processing circuitry 208. A user interface, such as user interface 306 described in FIG. 3, can receive the input representative of the stimulation efficacy. In some examples, the plurality of stimulation parameters defined in stimulation parameter settings 220 can include at least two of: a pulse frequency, a pulse width, an amplitude, electrode combination, an intra-pulse interval, a burst frequency, a burst duration, a duty cycle, a charge per second, or a waveform shape.

In some examples, the stored relationships between a plurality of stimulation parameters (e.g., stimulation parameter relationship data 224) can define changes to respective values of at least one stimulation parameter of the plurality of stimulation parameters between a first zone, a second zone, and a third zone of stimulation intensity. These different zones of intensity may specify increasing intensities and increasing power consumption. Therefore, in some examples, processing circuitry 208 may start with a first zone having a low intensity and iteratively try the second and third zones as needed to achieve effective therapy. The first zone can have a pulse frequency range between approximately 1 Hz and approximately 5 kHz or between approximately 1 Hz and 3 kHz and can have a pulse width range between approximately 0.01 ms and approximately 0.1 ms or between approximately 0.01 ms and approximately 0.05 ms. In one example, the first zone may have a pulse frequency between approximately 10 Hz and 1 kHz and a pulse width of approximately 0.03 ms. The second zone can have a pulse frequency range between approximately 1 Hz and approximately 5 kHz or between approximately 1 Hz and 3 kHz and can have a pulse width range between approximately 0.1 ms and approximately 1.0 ms or between approximately 0.1 ms and approximately 0.5 ms. In one example, the second zone may have a pulse frequency between approximately 10 Hz and 1 kHz and a pulse width of approximately 0.24 ms. The third zone can have a pulse frequency range between approximately 1 kHz and approximately 15 kHz or between approximately 3 kHz and approximately 12 kHz and can have a pulse width range between approximately 0.01 ms and approximately 0.1 ms or between approximately 0.1 ms and approximately 0.5 ms. In one example, the third zone may have a pulse frequency between approximately 5 kHz and 10 kHz and a pulse width of approximately 0.03 ms.

In some examples, the number of zones can be more or less than three zones (such as two zones, four zones, or five or more zones), and the parameter values of the zones may be lower or greater. Although each zone may have at least partially overlapping parameter value ranges, each zone may be specified to generally define a different level of intensity. For example, even if a pulse frequency may be selected to be the same in two different zones, one zone may specify a longer pulse width, or pulse width range, that results in a greater charge delivery. In addition, processing circuitry 208 may select a parameter value within a range if specified by the zone. Since increasing levels of intensity generally consume more power by stimulation generator 204, processing circuitry 208 may iteratively switch to higher zones of intensity only when needed to achieve more efficacious therapy.

Processing circuitry 208 can select the parameter values of the zones according to different guidelines, such as predefined relationships between two or more parameters specified by each zone. For example, processing circuitry 208 can select the second value of at least one of the first stimulation parameter or the second stimulation parameter to be within the second zone in response to the efficacy of the first electrical stimulation being insufficient. Processing circuitry 208 can also select the stimulation parameter values from at least one of the second zone or the third zone based on the stimulation parameter values selected for the first zone. In addition, processing circuitry 208 can identify stimulation parameter values defined by electrical stimulation with increasing levels of charge between each zone.

Processing circuitry 208 can process a received ECAP signal and determine a relationship between the received ECAP signal and the plurality of stimulation parameters (e.g., correlation data 228) to store in memory 216. In some examples, the second value of at least one of the first stimulation parameter or the second stimulation parameter can be set based upon on the relationship between the received ECAP signal and the plurality of stimulation parameters. In some examples, the plurality of stimulation parameters can include a first stimulation pulse frequency, and based on the relationships between the received ECAP signal and the plurality of stimulation parameters including the first stimulation pulse frequency, processing circuitry 208 can select a second, higher pulse frequency. In some examples, processing circuitry 208 can maintain stimulation intensity while changing at least one of the first stimulation parameter or the second stimulation parameter in an attempt to achieve increased therapy efficacy for the patient.

When selecting stimulation parameters, processing circuitry 208 can select stimulation parameters according to a strength-duration curve. For example, processing circuitry 208 can select values of a pulse frequency or pulse width to maintain intensity below the strength duration curve so that the patient does not perceive the stimulation or perceive discomfort from the electrical stimulation, as specified by the strength duration curve. The strength duration curve may be generated based on the combination of stimulation parameter values that result in the patient perceiving the stimulation, result in motor activity of the patient, or result in discomfort from the stimulation. Processing circuitry 208 can also select parameter values to reduce power consumption. For example, processing circuitry 208 can select the plurality of stimulation parameters according to the stored relationship between the plurality of stimulation parameters (e.g., stimulation parameter relationship data 224) to maintain stimulation efficacy while reducing power consumption. For example, long pulse widths or very high pulse frequencies can result in increased power consumption when compared with moderate pulse widths and moderate pulse frequencies.

Processing circuitry 208 can control delivery of a first electrical stimulation within a first zone of a plurality of intensity zones to a patient. In some examples, the first zone can have a first pulse frequency range and a first pulse width range. The first zone can be defined by other stimulation parameters as well, such as pulse amplitude, waveform shape, bursts of pulses, etc. In some examples, processing circuitry 208 can determine that the first electrical stimulation provides ineffective therapy for the patient (e.g., via patient input or sensed physiological data such as ECAP values). In response to determining that the first electrical stimulation provides ineffective therapy for the patient, processing circuitry 208 can select a second pulse frequency value from a second pulse frequency range of a second zone of the plurality of intensity zones and a second pulse width value from a second pulse width range of the second zone. In some instances, at least one of the second pulse frequency range can be greater than the first pulse frequency range or the second pulse width range can be greater than the first pulse width range. The stimulation parameter values selected from the second zone can define a second electrical stimulation having a second stimulation intensity greater than a first stimulation intensity of the first electrical stimulation. Processing circuitry 208 can also control delivery (e.g., provide instructions to stimulation generator 204) of the second electrical stimulation to the patient.

In some examples, a patient may not be responsive to either a first or second electrical stimulation. In response to determining that the second electrical stimulation provides ineffective therapy for the patient, processing circuitry 208 can select a third pulse frequency value from a third pulse frequency range of a third zone of the plurality of intensity zones and a third pulse width value from a third pulse width range of the third zone. In some examples, at least one of the third pulse frequency range can be greater than the second pulse frequency range or the third pulse width range can be less than the second pulse width range. The stimulation parameter values selected from the third zone can define a third electrical stimulation that has a third stimulation intensity greater than the second stimulation intensity of the second electrical stimulation. Similar to the first and second electrical stimulation, processing circuitry 208 can control delivery of the third electrical stimulation to the patient. The first, second and third zone may have one or more parameter values that are the same or substantially similar, as described herein. In some examples, the number of zones can be more or less than three zones (such as two or five zones), and the parameter values defined by each of the zones may be lower or greater.

Processing circuitry 208 can store relationships between the stimulation parameter values selected from the first zone and second zone (e.g., stimulation parameter relationship data 224). In some examples, the stored relationships can define how to change values of stimulation parameters when changing between zones, e.g., between the first zone and the second zone or between the first zone and the third zone.

Figure 3:
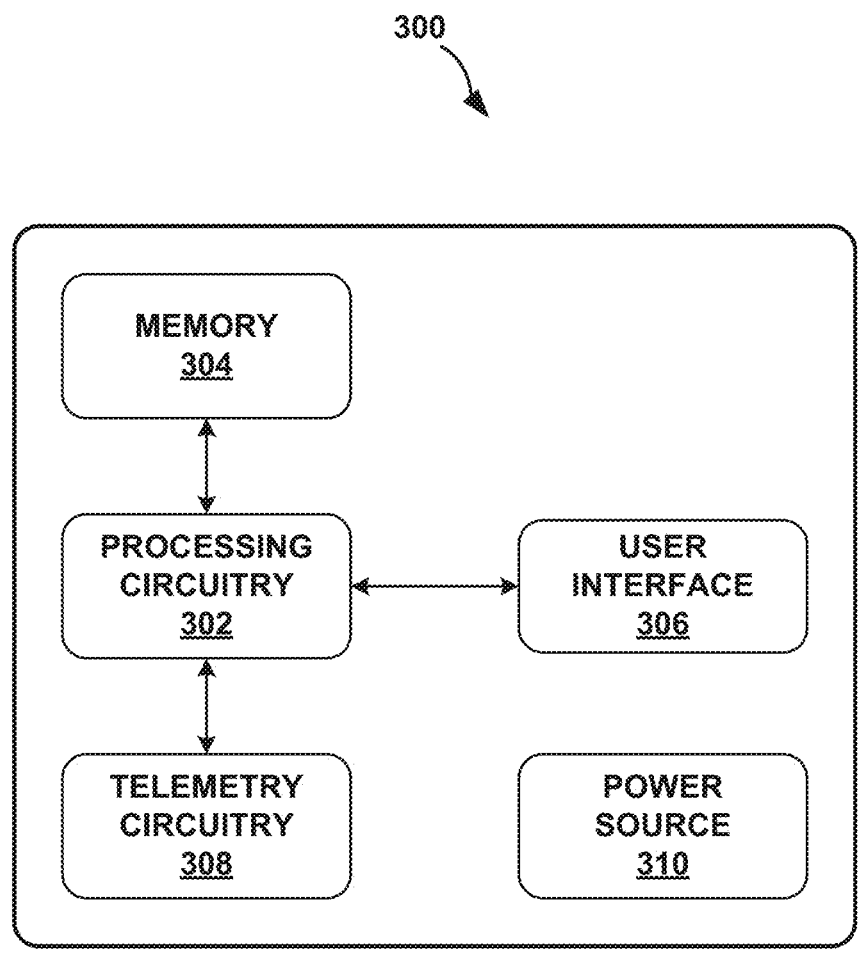
FIG. 3 is a block diagram of the example external programmer of FIG. 1.

FIG. 3 is a block diagram of the example external programmer 300. External programmer 300 may be an example of external programmer 104 of FIG. 1. Although programmer 300 may generally be described as a hand-held device, programmer 300 may be a larger portable device or a more stationary device. In addition, in some examples, programmer 300 may be included as part of an external charging device or include the functionality of an external charging device. As illustrated in FIG. 3, programmer 300 may include a processing circuitry 302, memory 304, user interface 306, telemetry circuitry 308, and power source 310. Each of these components, circuitry, or modules, may include electrical circuitry that is configured to perform some, or all of the functionality described herein. For example, processing circuitry 302 may include processing circuitry configured to perform the processes discussed with respect to processing circuitry 302.

In general, programmer 300 comprises any suitable arrangement of hardware, alone or in combination with software and/or firmware, to perform the techniques attributed to programmer 300, and processing circuitry 302, user interface 306, and telemetry circuitry 308 of programmer 300. In various examples, programmer 300 may include one or more processors, such as one or more microprocessors, DSPs, ASICs, FPGAs, or any other equivalent integrated or discrete logic circuitry, as well as any combinations of such components. Programmer 300 also, in various examples, may include a memory 304, such as RAM, ROM, PROM, EPROM, EEPROM, flash memory, a hard disk, a CD-ROM, comprising executable instructions for causing the one or more processors to perform the actions attributed to them. Moreover, although processing circuitry 302 and telemetry circuitry 308 are described as separate, in some examples, processing circuitry 302 and telemetry circuitry 308 are functionally integrated. In some examples, processing circuitry 302 and telemetry circuitry 308 correspond to individual hardware units, such as ASICs, DSPs, FPGAs, or other hardware units.

Memory 304 (e.g., a storage device) may store instructions that, when executed by processing circuitry 302, cause processing circuitry 302 and programmer 300 to provide the functionality ascribed to programmer 300 throughout this disclosure. For example, memory 304 may include instructions that cause processing circuitry 302 to obtain a stimulation parameter setting from memory, select a spatial electrode movement pattern, or receive a user input and send a corresponding command to programmer 300, or instructions for any other functionality. In addition, memory 304 may include a plurality of stimulation parameter settings, where each setting includes a parameter set that defines electrical stimulation. Memory 304 may also store data received from a medical device (e.g., IMD 110). For example, memory 304 may store ECAP related data recorded at a sensing circuitry of the medical device, and memory 304 may also store data from one or more sensors of the medical device.

User interface 306 may include a button or keypad, lights, a speaker for voice commands, a display, such as a liquid crystal (LCD), light-emitting diode (LED), or organic light-emitting diode (OLED). In some examples the display may be a touch screen. User interface 306 may be configured to display any information related to the delivery of electrical stimulation, identified patient behaviors, sensed patient parameter values, patient behavior criteria, or any other such information. Programmer 300 may receive user input via user interface 306. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation. In other examples, user interface 306 may receive input from the patient and/or clinician regarding efficacy of the therapy, such as binary feedback, numerical ratings, textual input, etc. In some examples, processing circuitry 302 may interpret patient requests to change therapy as negative feedback regarding the current parameter values used to define therapy.

Telemetry circuitry 308 may support wireless communication between the medical device and programmer 300 under the control of processing circuitry 302. Telemetry circuitry 308 may also be configured to communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna.

Examples of local wireless communication techniques that may be employed to facilitate communication between programmer 300 and IMD 110 include RF communication according to the 802.11 or Bluetooth specification sets or other standard or proprietary telemetry protocols. In this manner, other external devices may be capable of communicating with programmer 300 without needing to establish a secure wireless connection. As described herein, telemetry circuitry 308 may be configured to transmit a spatial electrode movement pattern or other stimulation parameter values to IMD 110 for delivery of electrical stimulation.

In some examples, selection of stimulation parameter settings may be transmitted to the medical device for delivery to the patient. In other examples, stimulation parameter settings may include medication, activities, or other instructions that the patient must perform themselves or a caregiver perform for the patient. In some examples, programmer 300 may provide visual, audible, and/or tactile notifications that indicate there are new instructions. Programmer 300 may require receiving user input acknowledging that the instructions have been completed in some examples.

According to the techniques of the disclosure, user interface 306 of external programmer 300 receives an indication from a clinician instructing a processor of the medical device to update one or more stimulation parameter settings or efficacy threshold settings. Updating stimulation parameter settings may include changing one or more parameter values of the electrical stimulation signal delivered by the medical device according to the settings, such as pulse amplitude, pulse width, pulse frequency, electrode combination, and/or waveform shape. Updating efficacy threshold settings can include increasing or decreasing the threshold for determining whether the electrical stimulation is effective. The efficacy threshold settings may be based upon sensed ECAP signals and stimulation parameter relationship data, in some examples. User interface 306 may also receive instructions from the clinician commanding any electrical stimulation. In some examples, the efficacy threshold may relate to a certain efficacy rating provided by the patient input in determining whether or not the therapy is effective (e.g., an efficacy threshold may be a rating of 6 on a scale of 1 to 10, where 10 is complete efficacy).

Power source 310 delivers operating power to various components of programmer 300. Power source 310 may be the same as or substantially similar to power source 214.

The architecture of programmer 300 illustrated in FIG. 3 is shown as an example. The techniques as set forth in this disclosure may be implemented in the example programmer 300 of FIG. 3, as well as other types of systems not described specifically herein. Nothing in this disclosure should be construed so as to limit the techniques of this disclosure to the example architecture illustrated by FIG. 3.

Figure 4:
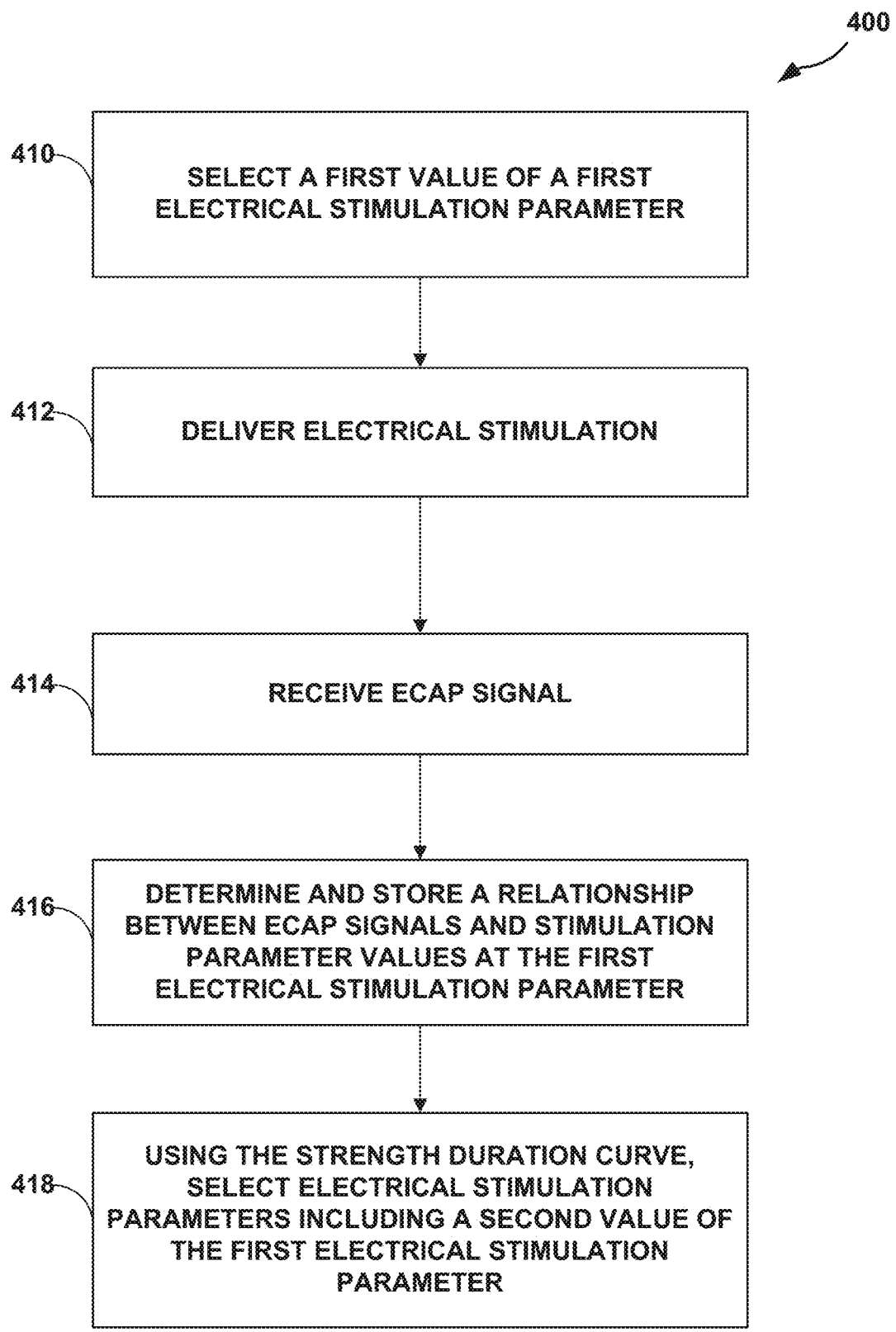
FIG. 4 is a flowchart illustrating an example technique for therapy delivery according to the techniques of this disclosure.

FIG. 4 is a flow diagram of an example technique for selecting stimulation parameter values. FIG. 4 will be described with processing circuitry 208 of IMD 200, but other devices such as IMD 110 or programmer 300 may perform similar functions. Besides IMD 200, an external programmer, e.g., external programmer 104 may be used alone or conjunction with one or more other medical devices, e.g., IMD 110 or 200, to determine and set stimulation parameters.

More particularly, FIG. 4 illustrates method 400 in which processing circuitry 208 selects the electrical stimulation parameters (410) including a first value of a first electrical stimulation parameter. The selection of electrical stimulation parameters may include the selection of values for additional values as well. Processing circuitry 208 can instruct stimulation generator 204 to produce stimulation for IMD 110 to deliver electrical stimulation according to the selected parameter values (412). Sensing circuitry 206 can sense an ECAP signal, and then processing circuitry 208 can receive the ECAP signal (414). Processing circuitry 208 then determines and stores a value indicative of the ECAP signal in memory 216, including the relationship between ECAP signals and the current stimulation parameter values used to generate the delivered stimulation (416). Using the strength duration curve, and in some instances in conjunction with the stored relationship between ECAP signals and stimulation parameter settings, processing circuitry 208 can select electrical stimulation parameters including a second value of the first electrical stimulation parameter (418). For example, processing circuitry 208 may select a pulse frequency value that corresponds, based on the predefined relationship to pulse width, to the pulse width selected to attempt to increase therapy efficacy. Two or more second values for electrical stimulation parameters may be selected. For example, first values for a first set of electrical stimulation parameters may not reach a threshold of efficacy. In response, processing circuitry 208 may select a second set of electrical stimulation parameter including a second value for more than one electrical stimulation parameter (e.g., pulse width and pulse frequency) to achieve an acceptable level of efficacy. The strength duration curve between at least two parameters may be generated for the patient at a prior time, such as during an initial programming session for IMD 200.

In some examples, an acceptable level of efficacy may be obtained with a first set of electrical stimulation parameters. In order to maintain the effective electrical stimulation efficacy and to continue determining the relationship between ECAP signals and stimulation parameter settings, processing circuitry 208 may select a second value for more than one electrical stimulation parameter. A second set of electrical stimulation parameters may be selected to achieve a higher or lower level of efficacy compared to a first set of electrical stimulation parameters. For example, a pulse frequency may be raised or lowered based on the relationship between ECAP signals and multiple stimulation parameter settings to achieve or maintain a level of electrical stimulation efficacy.

Figure 5:
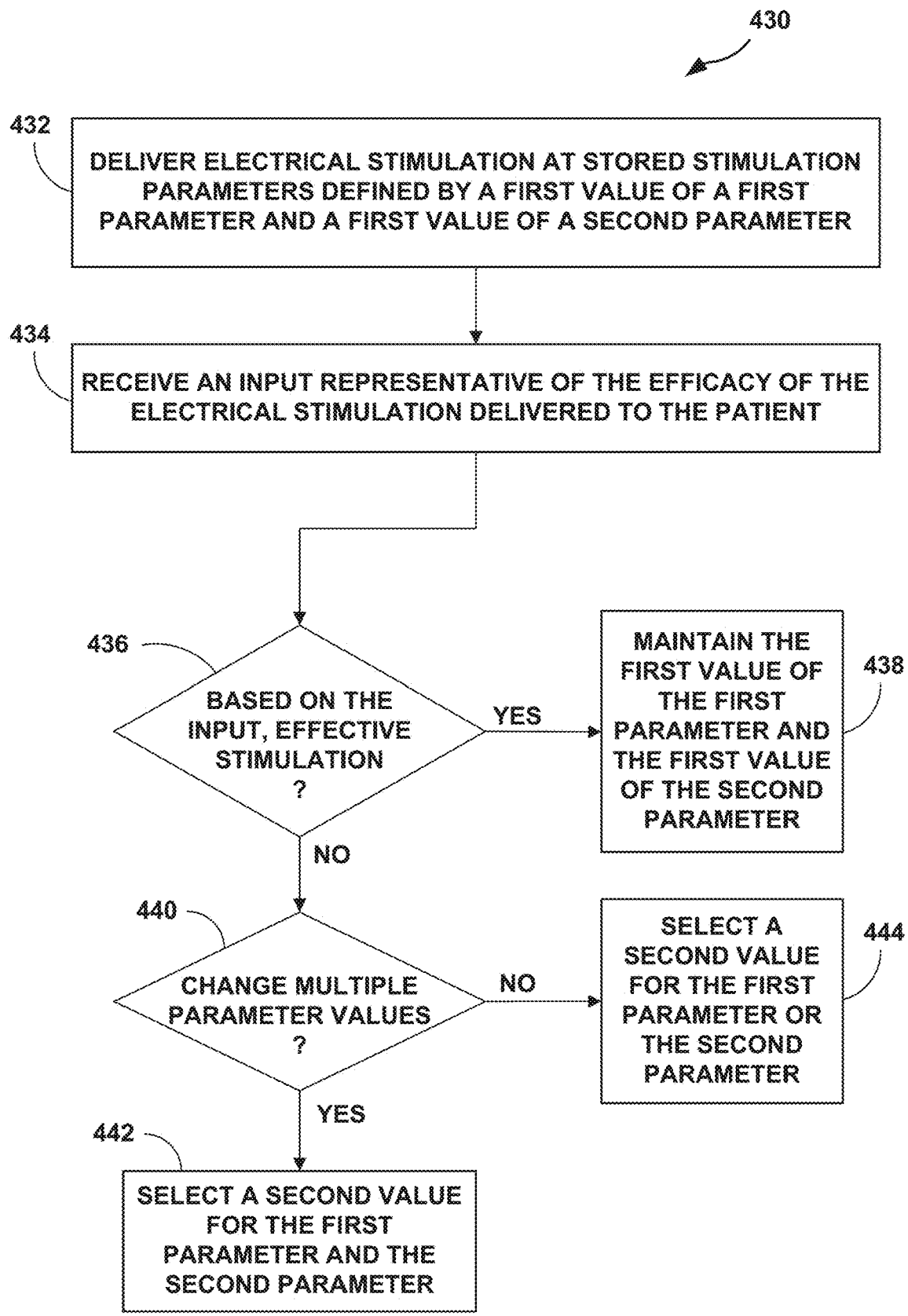
FIG. 5 is a flowchart illustrating an example technique for therapy delivery according to the techniques of this disclosure.

FIG. 5 is a flow diagram of an example technique for selecting stimulation parameters to achieve effective stimulation therapy. FIG. 5 will be described with respect to processing circuitry 208 of IMD 200, but IMD 110 or other device may perform similar functions in other examples. Besides the IMD, an external programmer, e.g., external programmer 104 may be used alone or in conjunction with one or more other medical devices, e.g., IMD 110 or 200, to determine and set stimulation parameters.

More particularly, FIG. 5 illustrates method 430 in which stimulation generator 204 delivers electrical stimulation according to stored stimulation parameters defined at least by a first value of a first parameter and a first value of a second parameter (432). Sensor 210 may receive an input representative of the efficacy of the electrical stimulation delivered to the patient (434). Based on the input, if processing circuitry 208 determines that the electrical stimulation delivered to the patient was effective ("YES" branch of block 436), processing circuitry 208 can maintain the first value of the first parameter and the first value of the second parameter for continued delivery of stimulation. In some examples, electrical stimulation may be determined to be effective by detecting target ECAP characteristic values (e.g., values of the ECAP indicative of target stimulation intensity) or receiving an input representative of the efficacy of the electrical stimulation according to stimulation parameter values. Target ECAP characteristic values can also include the relationship between ECAP signals and stimulation parameters. Alternatively, if processing circuitry 208 determines that the electrical stimulation delivered to the patient was ineffective ("NO" branch of block 436), processing circuitry 208 can determine whether to change multiple parameter values (440). If processing circuitry 208 determines to change one parameter value ("NO" branch of block 440), then processing circuitry can select a second value for the first parameter or the second parameter (444). In the alternative, if processing circuitry 208 determines to change multiple parameter values ("YES" branch of block 442), processing circuitry 208 can select a respective second value for the first parameter and the second parameter (442). In some examples, processing circuitry 208 can select a second value for more than two parameters when adjusting the values of multiple parameters. Moreover, processing circuitry 208 may select the new values for the one or more stimulation parameters according to predetermined relationships between two or more parameters.

Figure 6:
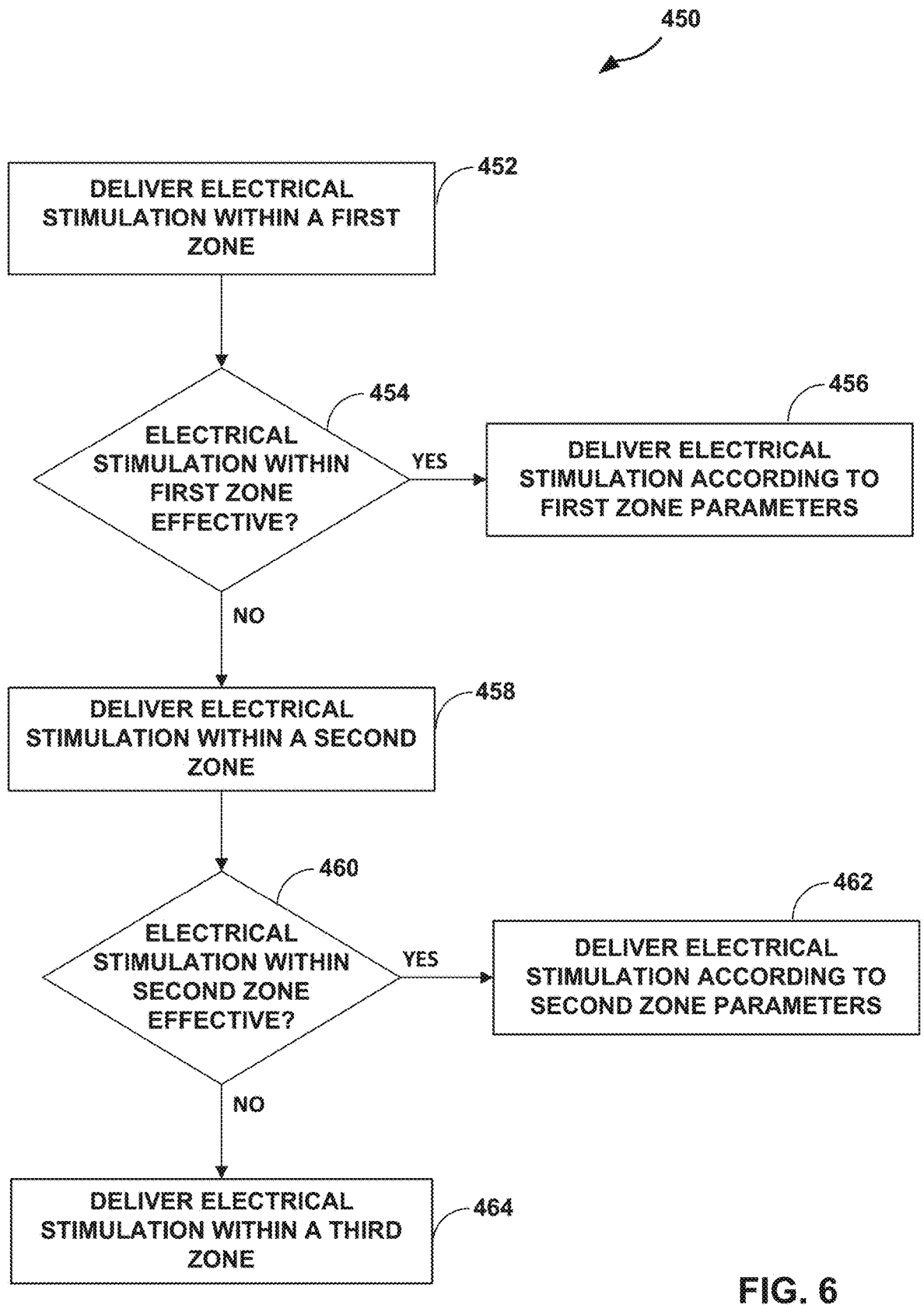
FIG. 6 is a flowchart illustrating an example technique for therapy delivery according to the techniques of this disclosure.

FIG. 6 is a flow diagram of an example technique for selecting stimulation parameters according to different zones of stimulation intensity. Example FIG. 6 will be described with respect to processing circuitry 208 of IMD 200, but other devices such as IMD 110 may perform similar functions. Besides IMD 200, an external programmer, e.g., external programmer 104 may be used alone or conjunction with one or more other medical devices, e.g., IMD 110 or 200, to determine and set stimulation parameters.

More particularly, FIG. 6 illustrates method 450 in which stimulation generator 204 delivers electrical stimulation within a first zone (452). The first zone may specify a first set of stimulation parameters that may include a range of acceptable values for at least one parameter. Processing circuitry 208 will determine whether the electrical stimulation within the first zone was effective (454). For example, processing circuitry 208 may determine efficacy from patient input and/or sensed data such as ECAP signals. If processing circuitry 208 determines electrical stimulation was effective within the first zone ("YES" branch of block 454), processing circuitry 308 will continue to control stimulation generator 204 to deliver electrical stimulation according to first zone parameters (456). If processing circuitry 208 determines electrical stimulation within the first zone was not effective ("NO" branch of block 454), processing circuitry 208 will control stimulation generator 204 to deliver electrical stimulation within a second zone (458). The second zone may define a different value for at least one stimulation parameter than the first zone. The second zone may define stimulation intensity generally greater than the stimulation deliverable according to the first zone.

Processing circuitry 208 will then determine whether the electrical stimulation according to the second zone was effective (460). If processing circuitry 208 determines electrical stimulation was effective within the second zone ("YES" branch of block 460), processing circuitry 208 will continue to control stimulation generator 204 to deliver electrical stimulation according to second zone parameters (462). If processing circuitry 208 determines electrical stimulation within the second zone was not effective ("NO" branch of block 460), processing circuitry 208 will control stimulation generator 204 to deliver electrical stimulation according to a third zone (464). The third zone may define a different value for at least one stimulation parameter than the second zone. The third zone may define stimulation intensity generally greater than the stimulation deliverable according to the second zone. In addition, processing circuitry 208 can determine to move up or down by more than one zone. For example, after processing circuitry 208 determines that electrical stimulation within the first zone was not effective, processing circuitry 208 can control stimulation generator 204 to deliver electrical stimulation within the third zone. The second zone may be skipped in some examples when processing circuitry 208 determines the electrical stimulation within the first zone did not reach a threshold level of electrical stimulation efficacy and the second zone intensity will likely not be effective. In other examples, processing circuitry 208 may change parameter values within a zone for one or more iterations (e.g., changing a value of a parameter that includes a range of values) in an attempt to identify effective therapy before moving to another zone.

The parameters selectable for defining SCS include, for example, pulse frequency, pulse-width, pulse amplitude, intra-pulse interval, electrode combination (e.g., operative electrodes and polarity of each electrode) and/or waveform shape. These parameters are not fully separate and independent, since therapy efficacy is dependent on the combination of each parameter. There may be a detectable relationship among at least some of the above parameters. If SCS is delivered through charge dosing strategies, all parameters may be considered to contribute to the calculation of charge over time (e.g., charge per second). Therefore, known relationships between different stimulation parameters may be leveraged when selecting parameter values to modulate pain pathways within the nervous system.

In some examples, processing circuitry may utilize sensory responses to neuromodulation can be to titrate stimulation parameters across different therapy fields, e.g., sacral nerve stimulation on bladder or bowl control, DBS on dystonia as well as SCS for pain management. For example, processing circuitry may use objective markers of electromyography (EMG) responses to neuromodulation to evaluate parameter value selection, such as electrode combination, pulse width, pulse frequency, and the like. Motor responses from EMG data can be used to achieve effective SCS lead placement intraoperatively since a patient's ability to discriminate sensation can be less reliable under sedation. Although EMG is described as a feedback input for stimulation, metrics such as ECAP values or other measures may be used in other examples.

FIGS. 7A through 11D provide illustrations of data collected from stimulation delivered to anesthetized rats according to various techniques described herein. Similar responses may be achieved in other species, such as humans. However, values for one or more stimulation parameters may be different for different species, and measured signals (e.g., EMG or ECAP) may vary in amplitude and/or delay To obtain the data illustrated in the examples of FIGS. 7A through 11D, female Sprague-Dawley rats (n=24) weighing 200-300 g were anesthetized with urethane (two intraperitoneal injections, 4 minutes apart, total 1.2 g/kg). During surgery (for implantation of SCS electrodes), anesthesia was maintained with supplemental dose of 1-2% isoflurane (Forene® available from Abbott, Solna, Sweden) in a 1:1 mixture of air and oxygen at a flow rate of 2 L/min. The level of anesthesia was frequently monitored by assessing the size of the pupils, general muscle tone, and withdrawal responses of the subject to noxious stimulation. During data collection, urethane anesthetized rats were maintained at 37° C. with a heating pad and were euthanized by $CO_2$ asphyxia upon completion of experimental procedures. All procedures were approved by the Institutional Animal Care and Use Committees of Medtronic and NAMSA (Minneapolis, MN).

To deliver SCS, four-contact rodent leads (a miniature four-pole plate lead; pole diameter 0.9-1.0 mm; center spacing 1.8-2.0 mm; available from Medtronic, Dublin, Ireland) were inserted in the rostral direction in the dorsal epidural space through a T13/L1 mini-laminectomy. The leads were placed at a position such that the active contacts were at the lumbar (~L3-L5) segments for SCS. To record the EMG response, wire electrodes were placed into the biceps femoris bilaterally. The EMG signals evoked in response to SCS were initially amplified through a low-noise AC differential amplifier (Model 1700, A-M Systems, Sequim, WA) with filter settings of 10-5000 Hz, gain X1000, and a sampling rate of 25 kHz. After surgery, the rats were allowed to recover for at least one hour before data collection.

The SCS was delivered using the Power 1401 CED data acquisition system (Cambridge, ENGLAND) and an isolation unit (Model 220, A-M Systems, Sequim, WA), which was connected to the externally tunneled SCS lead. A four-contact electrode (Medtronic Inc.) was used to provide bipolar SCS. The contacts were coupled bipolarly (+, −, +, − from rostral to caudal). The first and third contacts (rostral to caudal) of the four-contact lead were set as an anode, and the second and fourth were set as a cathode ("twin-pairs" stimulation). However, the stimulation and sense electrodes could be configured using leads having additional electrodes or electrodes with different distances between electrodes. The stimulation signals were programmed by CED Spike2 software (version 7.07, Cambridge, ENGLAND). The studied parameters included pulse frequency (PF), pulse width (PW), intra-pulse interval (IPI), pulse amplitude (PA), and waveform shapes (rectangle, ramp-down triangle, and ramp-up triangle). It is noted that intensity, as discussed herein, can be generated by a combination of pulse amplitude, pulse width, and pulse frequency, for example.

The groups of subjects included:
1) in 9 rats, the pulses were delivered as 1-s bursts in every 10 seconds with increased intensities from low to high. The 1-s bursts in each test set contained a fixed PF and PW. The examined parameters were PF (10 Hz, 50 Hz, 100 Hz, 200 Hz, 400 Hz, 500 Hz, 1 kHz, 5 kHz and 10 kHz) at 0.03 ms PW and 0.24 ms PW, and PW (0.03 ms, 0.06 ms, 0.09 ms, 0.12 ms, 0.15 ms, 0.18 ms, 0.21 ms, 0.24 ms, 0.27 ms and 0.3 ms) at 10 Hz and 200 Hz;
2) in other 9 rats, 10 Hz conditional stimulation (10 seconds) in each tested pulse amplitude were given before or after 1-s bursts; and
3) in additional 6 rats, the pulses were delivered as 1-s bursts in every 5 seconds with increased intensities from low to high. The parameter combinations of pulse frequency (10 Hz, 50 Hz, 200 Hz), pulse amplitude (0.1 ms, 0.3 ms, 1, 3 ms), intra-pulse interval (0, 0.1 ms, 0.3 ms), and waveform shapes (rectangle, ramp-down triangle, and ramp-up triangle) were programed.

Evaluated parameters of EMG response were threshold ($T_{EMG}$), e.g., intensity of the EMG signals, and the area under the curve (AUC, represented by mV-msec) of integrated and calculated EMG action potentials. As the basic unit of electrical stimulation, the pulse is delivered by current flow (current intensity, I) for a specific amount of time (PW, t). The amount of current flow may be constant (e.g., rectangle waveform) or increasing (e.g., ramp-up triangle) or decreasing (e.g., ramp-down triangle) in intensity. The charge per pulse is calculated as $\int Id(t)$. The charge per second is calculated by multiplying the charge per pulse by number of pulses delivered in 1 second (frequency).

Responses to SCS were plotted against the stimulation intensity. The $T_{EMG}$ of each individual response was defined as the intensity or charge per second (PA*PW*PF) at which evoked EMG potentials were distinguished from basal activity in the EMG detection window and increased to ascending intensities of consecutive stimuli.

Data were calculated and analyzed using analysis of variance (ANOVA) by Prism 5 (GraphPad Software, Inc., La Jolla, CA). Bonferroni post-test was used to determine the statistical significance between individual points. Correlations (group 3) among stimulation parameters were analyzed by mixed model using SAS program. All data was expressed as mean±SEM and a value of $p<0.05$ was considered statistically significant.

Figure 7A:
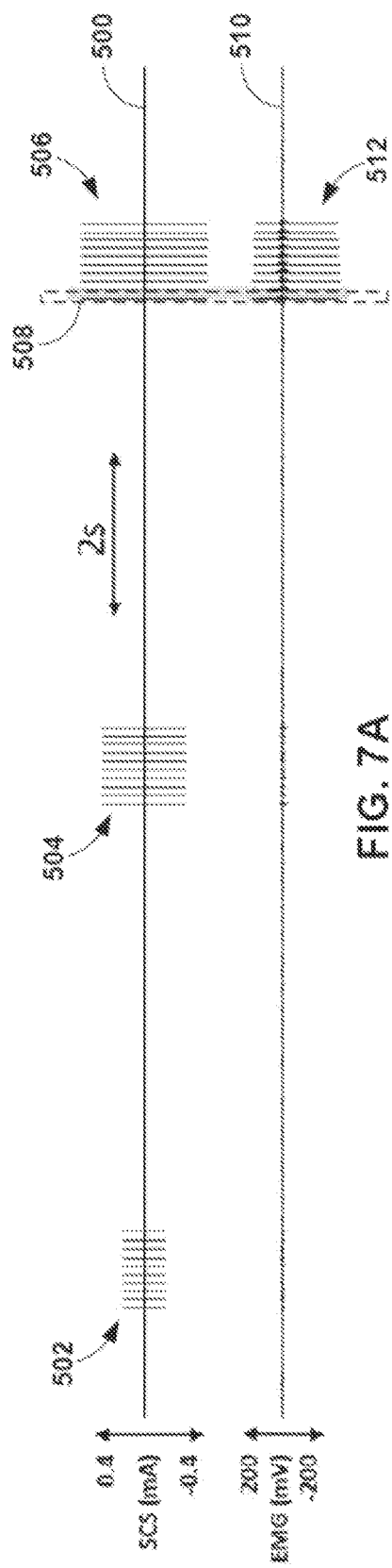
FIGS. 7A, 7B, 7C, and 7D are graphs of example raw traces of electromyograph (EMG, mV) responses to SCS.
Figure 7B:
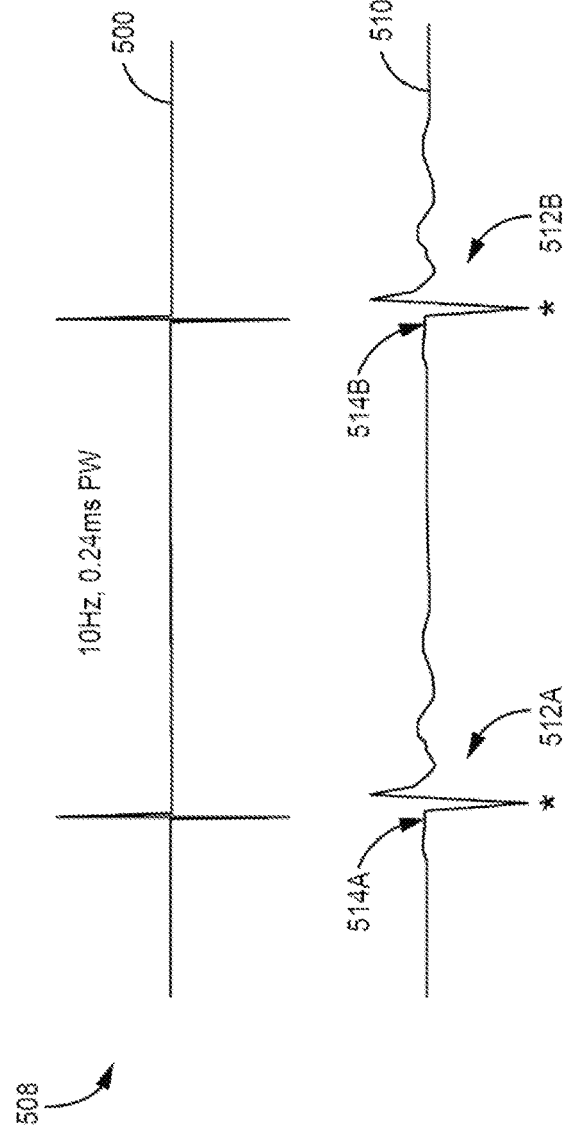
Figure 7C:
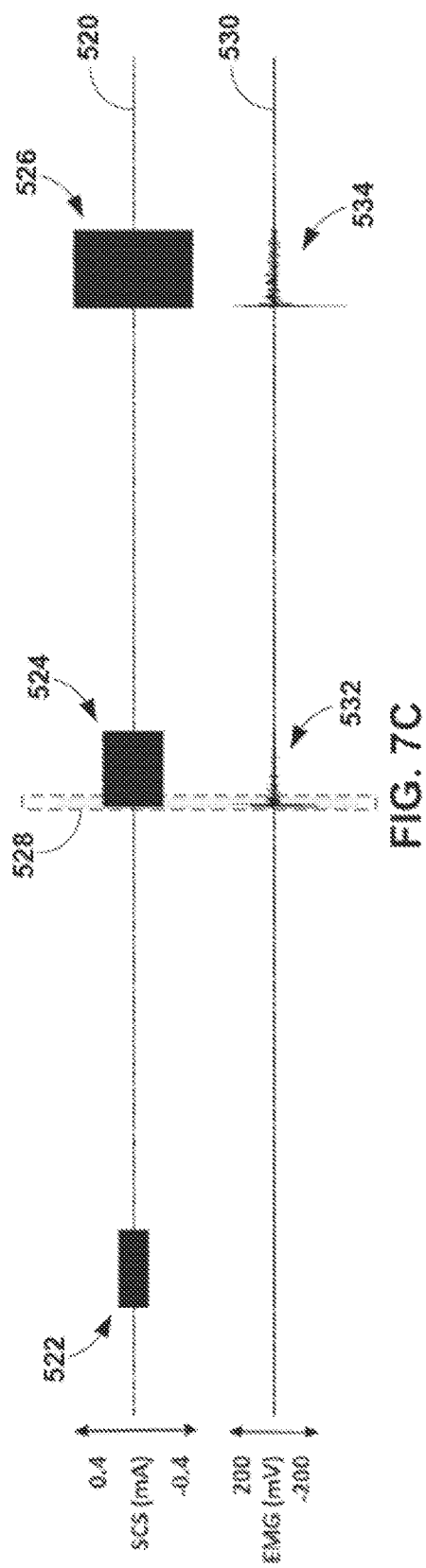
Figure 7D:
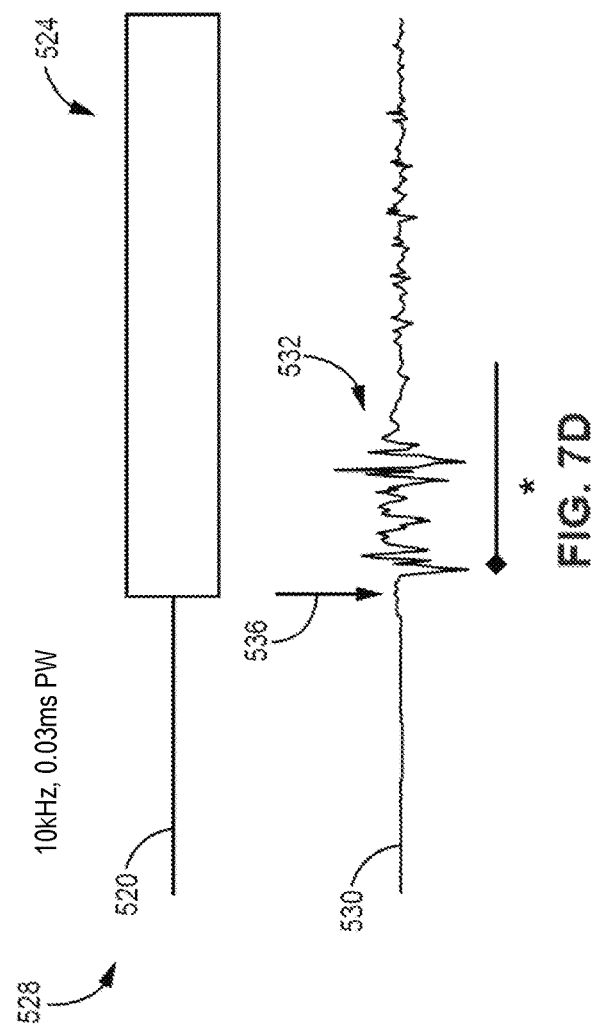

EMG responses generally increased with increasing SCS PA across all tested PFs and PWs. FIGS. 7A-7D are example raw traces of electromyograph (EMG, mV) responses to SCS. In the example of FIG. 7A, a 1 second burst SCS at 10 Hz and 0.24 ms pulse width was delivered every 5 seconds. Pulse bursts 502, 504, and 506 were delivered with increasing amplitudes, as shown by trace 500. However, evoked EMG signals on trace 510 were only detected in response to pulses from pulse burst 506, resulting in EMG signals 512. Shaded area 508 of pulse burst 506 and EMG signals 512 is shown in more detail in FIG. 7B. As shown in FIG. 7B, a duration of approximately 0.2 ms is shown with a recorded amplitude of up to 0.4 mA SCS. Each EMG waveform 512A and 512B was detected from corresponding pulses from pulse burst 506. Each arrow 514A and 514B indicate respective stimulus artifacts with a latency of approximately 3-4 ms when the PF was less than 100 Hz. In the example of FIG. 7C, a 1 second burst SCS at 10 kHz and 0.03 ms pulse width was delivered every 5 seconds. Pulse bursts 522, 524, and 526 were delivered with increasing amplitudes, as shown by trace 520. However, evoked EMG signals on trace 530 were only detected in response to pulses from pulse bursts 524 and 526, resulting in EMG signals 532 and 534, respectively. Shaded area 528 of pulse burst 524 and EMG signal 532 is shown in more detail in FIG. 7D because this was the lowest amplitude of pulses for which an EMG signal was detected. As shown in FIG. 7D, a duration of approximately 0.2 ms is shown with a recorded amplitude for pulse burst 524 of up to 0.2 mA SCS. When pulse frequency was more than 200 Hz, the latency (e.g., time between arrow 536 and first detected wave of EMG signal 532) and the duration of EMG waveform appeared to be longer than the time between two SCS pulses, so the initial group of evoked potentials in EMG signal 532 appeared to be sharp and strong post stimulation then decayed quickly even with continuous SCS as shown in graph 528 of FIG. 7D. The EMG responses were larger in amplitude as the stimulation intensity was increased. Such SCS evoked EMG signals disappeared after rats were euthanized.

Figure 8A:
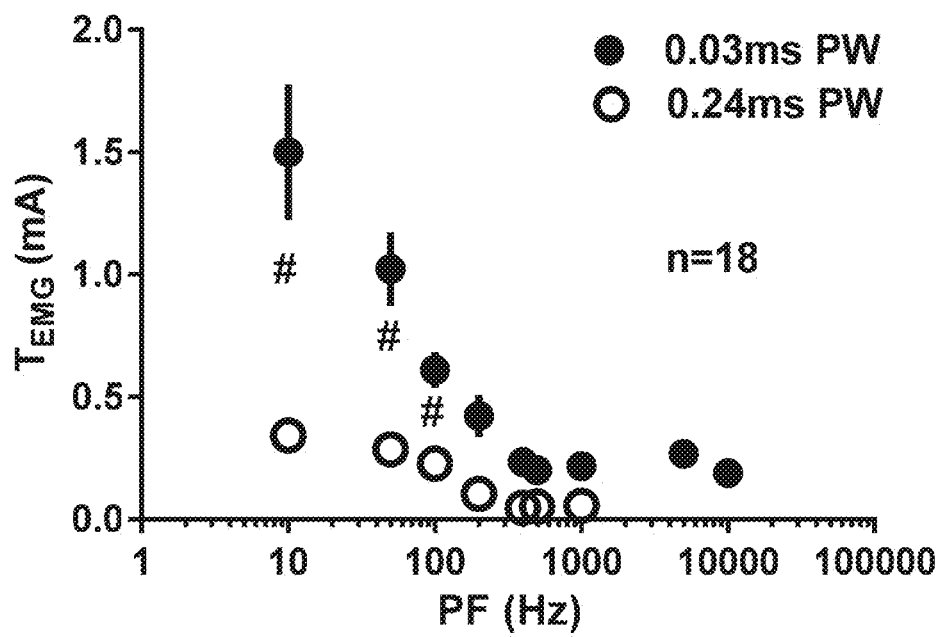
FIGS. 8A, 8B, 8C, and 8D are graphs illustrating example data of the threshold of electromyograph responses to different pulse frequencies of the SCS at pulse widths of 0.03 milliseconds (ms) and 0.24 ms.
Figure 8B:
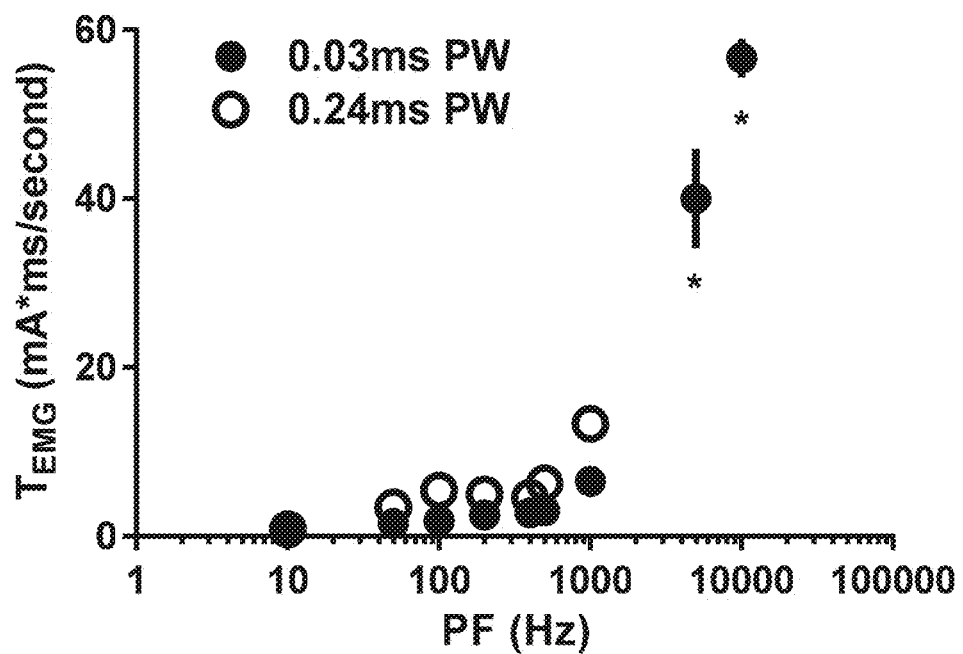
Figure 8C:
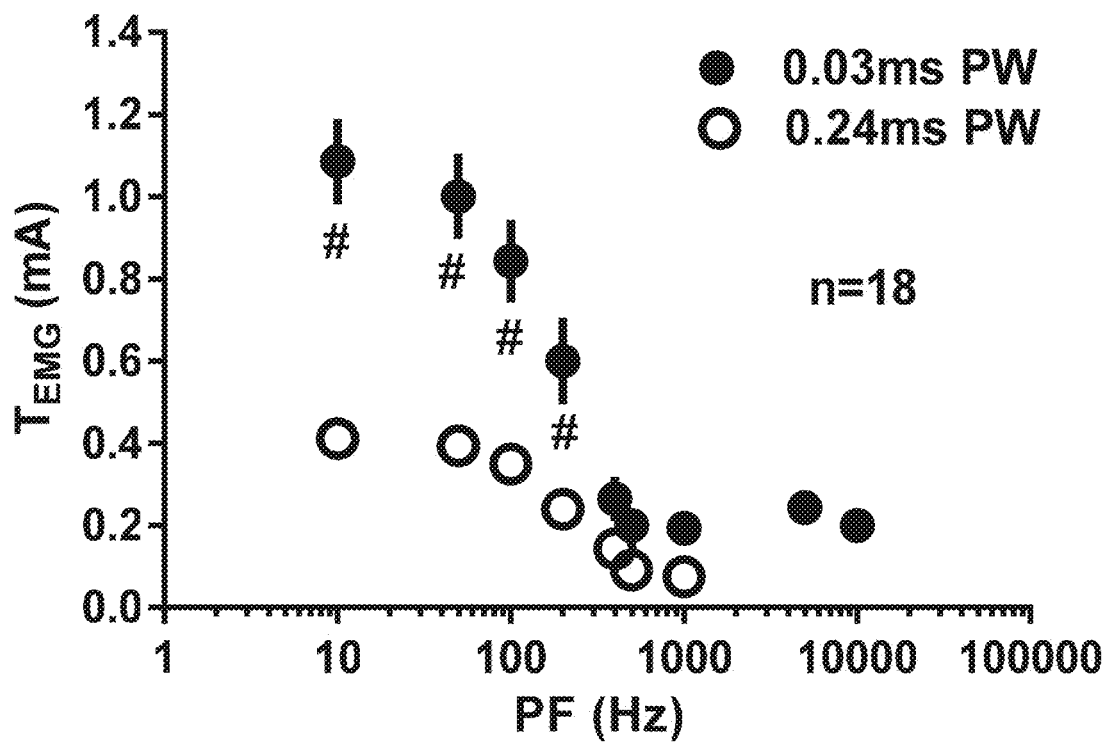
Figure 8D:
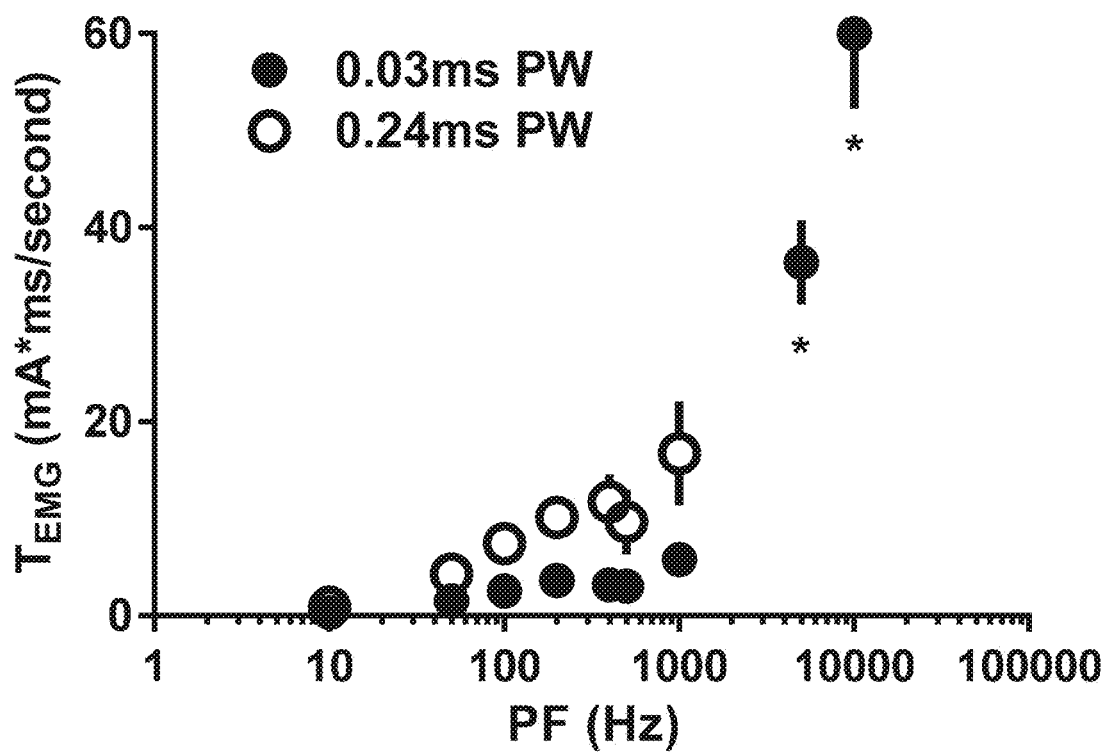

FIGS. 8A-D summarize example data of the threshold of electromyograph responses ($T_{EMG}$) to different pulse frequencies of the SCS at pulse widths of 0.03 ms and 0.24 ms. There were three charge levels to trigger EMG responses: 10 Hz-1 kHz and 0.03 ms PW<10 Hz-1 kHz and 0.24 ms PW<1 Hz-10 kHz and 0.03 ms PW. The 1-s burst of SCS was delivered without basal conditional stimulation (FIGS. 8A and 8B) or with 10 Hz basal conditional stimulation between bursts (FIGS. 8C and 8D). $T_{EMG}$s of SCS are expressed using pulse widths at mA (FIGS. 8A and 8C) or pulse charges per second (mA*ms/second), which are calculated by pulse amplitude, pulse width, and pulse frequency (FIGS. 8B and 8D). The absolute values (mA) of $T_{EMG}$ at 5 kHz and 10 kHz are less, but charges per second are greater than that at pulse frequency ≤1 kHz (indicated by *), p<0.05, ANOVA Bonferroni post test). There are also differences between $T_{EMG}$s expressed with mA or charge per second between 0.03 ms and 0.24 ms pulse width (indicated by #), 0.03 ms pulse width vs. 0.24 ms pulse width, p<0.05, ANOVA Bonferroni post test). In this manner, clinician could toggle between different pulse widths and pulse frequencies to achieve an expected intensity or amplitude of the threshold EMG response (or ECAP response) based on this relationship between different parameters.

The EMG response thresholds were pulse frequency and pulse width dependent. The relationship of EMG responses to different pulse frequencies or pulse widths of SCS remained the same whether 10 Hz conditional stimulations in each tested pulse amplitude were given or not. As the pulse frequency increased, the threshold expressed in pulse amplitude (mA) to SCS decreased (FIGS. 8A and 8C), but threshold in charge (mA*ms/second) increased (FIGS. 8B and 8D).

Figure 9A:
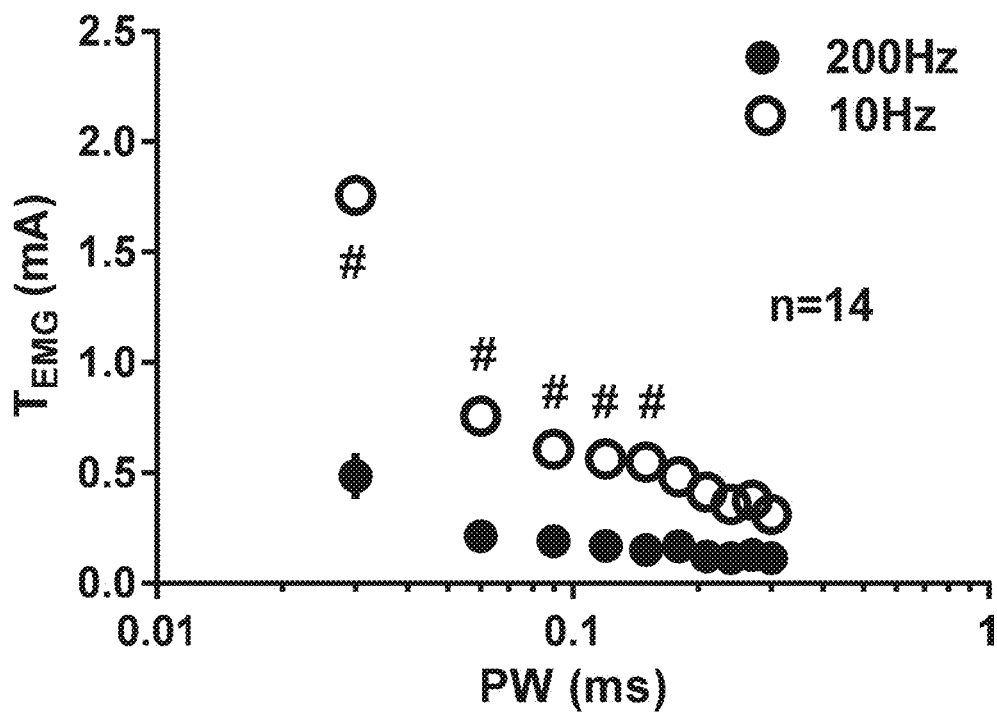
FIGS. 9A and 9B are graphs illustrating example data of the threshold of electromyograph responses to different pulse-widths of the SCS at pulse frequencies of 10 Hz and 200 Hz.
Figure 9B:
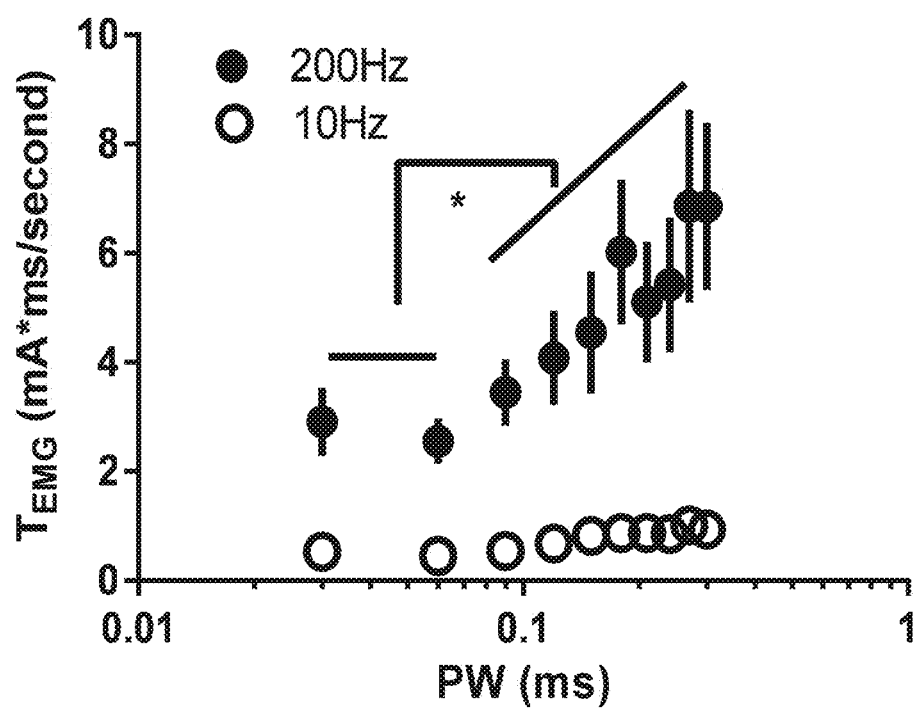

FIGS. 9A and 9B summarize example data $T_{EMG}$ calculated from different pulse-widths of the SCS at pulse frequencies of 10 Hz and 200 Hz. $T_{EMG}$s of SCS are expressed using pulse widths at mA (FIG. 9A) or current charges per second (mA*ms/second) (FIG. 9B), which are calculated by (pulse amplitude)*(pulse width)*(pulse frequency). There are statistical differences between $T_{EMG}$s expressed with mA between 200 Hz pulse frequency and 10 Hz pulse frequency as shown in FIG. 9A (indicated by #, p<0.05, ANOVA Bonferroni post test). There are also differences of $T_{EMG}$s expressed with charge per second between different pulse widths (indicated by *, p<0.05, ANOVA Bonferroni post test).

Response thresholds were pulse width dependent. As the pulse width increased, the threshold expressed in pulse amplitude (mA) to SCS decreased (FIG. 9A), but threshold in charge (mA*ms/second, FIG. 9B) increased. Longer pulse widths had higher charge delivery to evoke EMG responses, especially at higher pulse frequencies. Based on these relationships between pulse frequency and pulse width, parameter values maybe changed to achieve the same threshold values for amplitude or intensity, or to achieve expected threshold amplitudes or intensities when changing values.

Temporal summation, where multiple pulses build on each other to achieve neuronal activation, may be one of the mechanisms induced by using higher frequency pulses. To examine the temporal summation mechanism, the latency of EMG responses to different pulse amplitudes of the SCS were analyzed while pulse widths were 0.03 ms and 0.24 ms and pulse frequencies were greater than 200 Hz. FIGS. 10A-D illustrate example data corresponding to different latencies at different pulse frequencies or amplitudes.

Figure 10A:
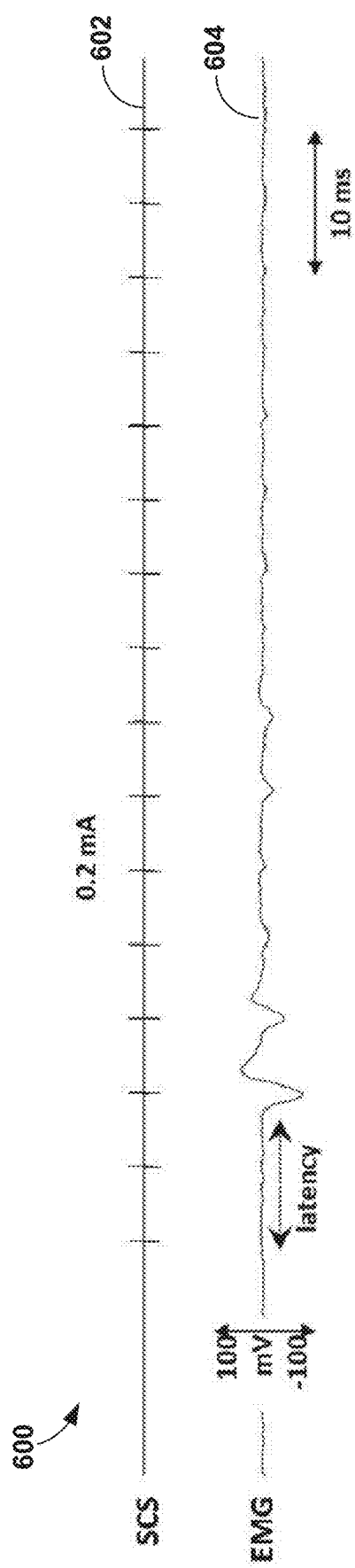
FIGS. 10A, 10B, 10C, and 10D are graphs illustrating of example latencies of EMG responses to different stimulation intensities of SCS at pulse widths of 0.03 ms and 0.24 ms when the pulse frequency was greater than 200 Hz.
Figure 10B:
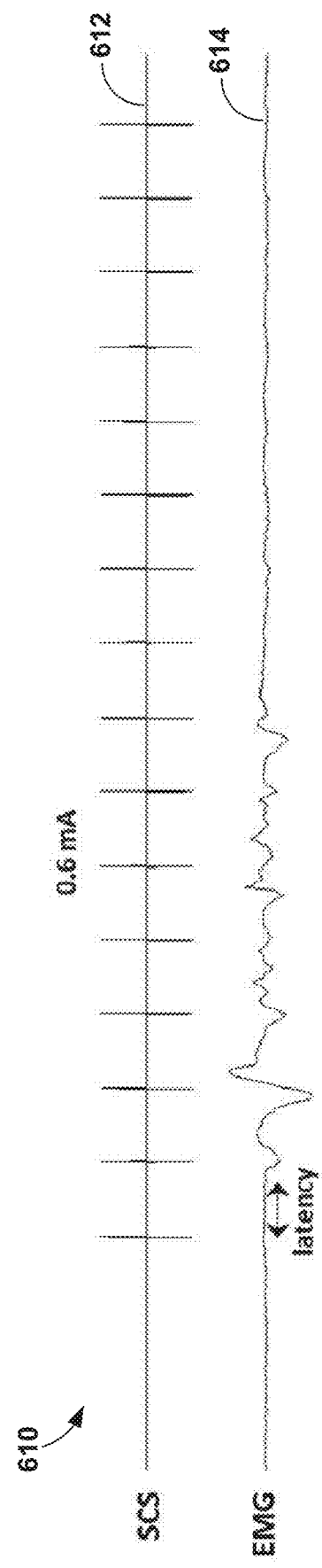

As shown in FIGS. 10A-D, example graphs of the latency of EMG responses to different stimulation intensities of SCS at pulse widths of 0.03 ms and 0.24 ms are provided when the pulse frequency was greater than 200 Hz. There were clear separations of response curves, which yielded three charge levels to trigger EMG responses: 200 Hz-1 kHz and 0.03 ms pulse width <200 Hz-1 kHz and 0.24 ms pulse width <5-10 kHz and 0.03 ms pulse width. However, other charge levels may exist for different locations, types of stimulation, or electrode combinations selected, for example. FIGS. 10A and 10B show exemplary raw traces of EMG (mV) responses to 200 Hz pulse frequency and 0.03 ms pulse width stimulation with pulse amplitude at 0.2 mA (graph 600 of FIG. 10A) and 0.6 mA (graph 610 of FIG. 10B) in the same rat. In FIG. 10A, the EMG responses in trace 604 could be triggered and measured following two pulses of 0.2 mA stimulation in trace 602 (latency of approximately 8 ms). However, in FIG. 10B, only one pulse of 0.6 mA stimulation in trace 614 triggered measurable EMG responses in trace 614 (latency of approximately 4 ms). In this manner, the larger charge of stimulation from trace 612 more quickly triggered the evoked response when compared with the smaller stimulation pulses of trace 602.

Figure 10C:
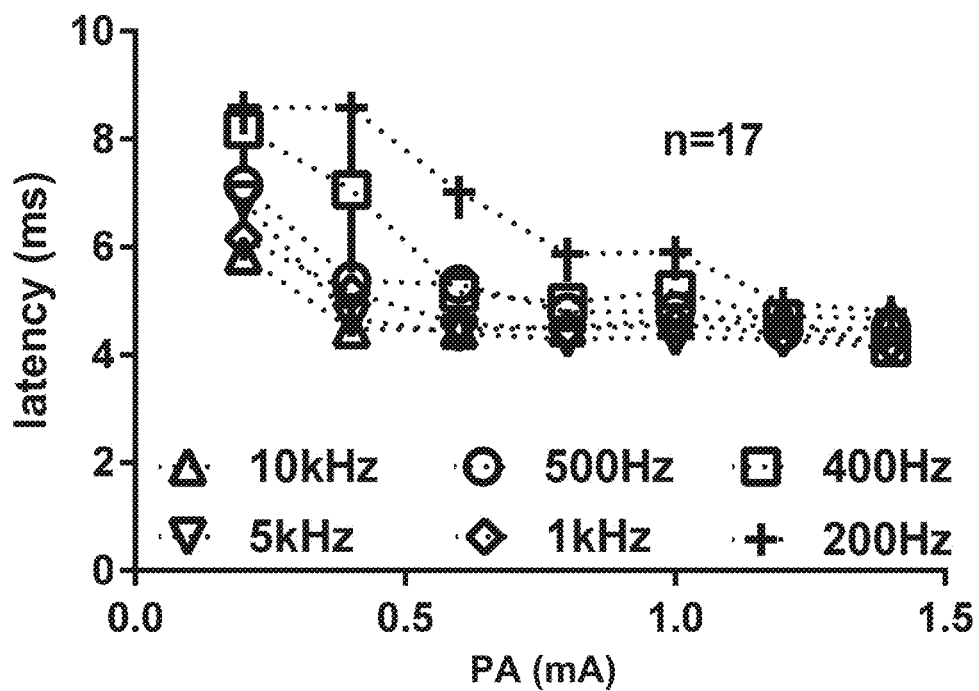
Figure 10D:
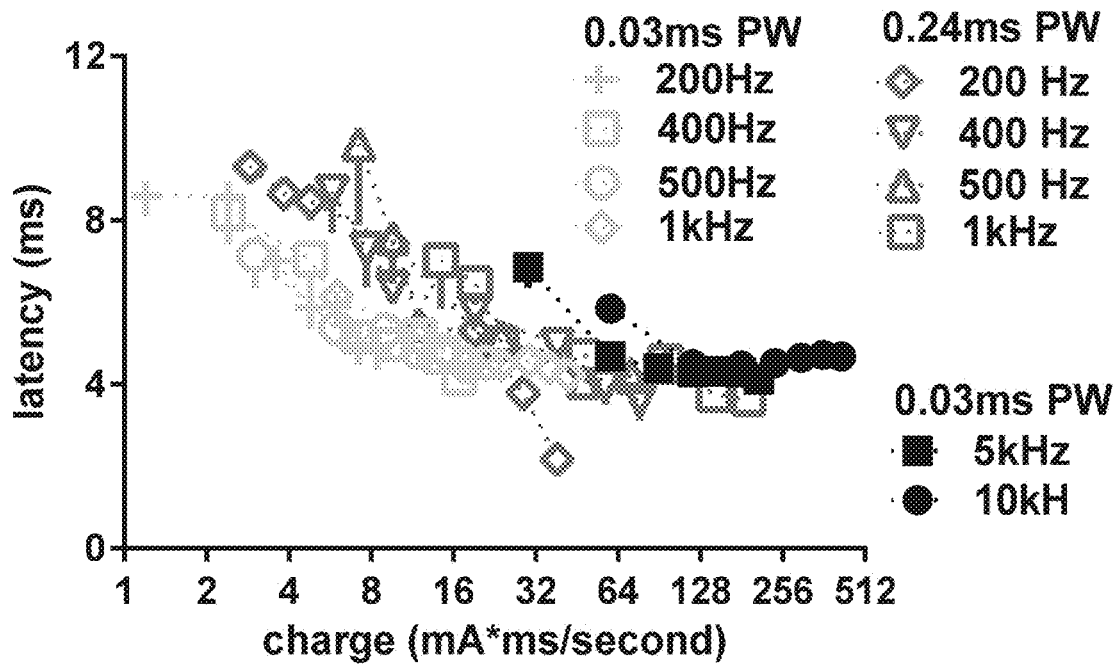

FIGS. 10C and 10D summarize data of the latency (ms) of EMG responses to SCS pulses where the pulse amplitude (pulse amplitude (PA), x-axis) is expressed by absolute values or current in mA (FIG. 10C) and current charge per second with mA*ms/second (FIG. 10D). The latency of EMG to SCS was charge (per second) dependent (FIG. 10D). In other words, larger charge from SCS resulted in shorter latency of EMG signals.

Based on this data, the evoked potentials appeared to be sharp and strong post stimulation then decayed quickly. As the pulse amplitude (PA) increased, the latency decreased. Analysis of latency-pulse amplitude (PA) responses revealed the latency saturated to the minimal of approximately 4 ms, which was similar to the latency when the pulse frequency was less than 100 Hz while action potentials couple well with stimulation artifacts and temporal summation was not applied, as shown in FIG. 10C. The slopes before reaching the plateau of the latency-pulse amplitude curves were slower when pulse frequencies were lower (fewer pulses in a given time unit). In other words, lower pulse frequencies generally resulted in less charge and higher latencies for similar pulse widths. As shown in FIG. 10D, increasing the frequency of pulses having the same pulse width generally reduced the latency towards the 4 ms saturation point.

Figure 11A:
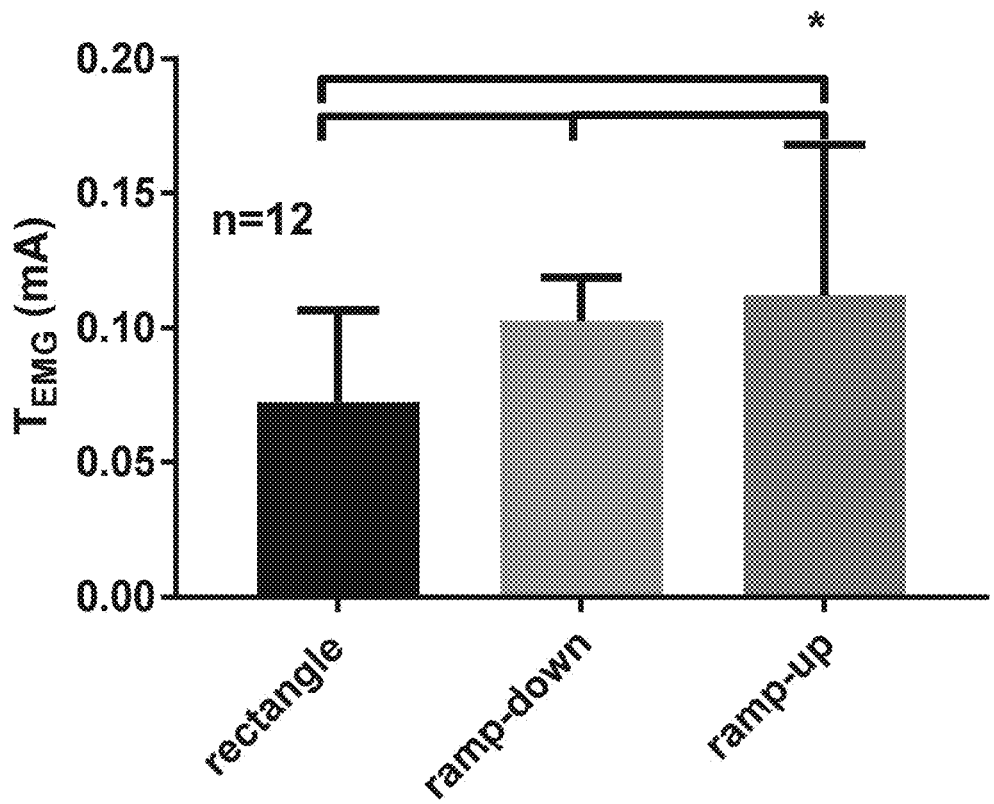
FIGS. 11A, 11B, 11C, and 11D are graphs illustrating example a mixed model analysis of relationships among different parameters of SCS to trigger amplitudes of electromyographs, including the impact different waveform shapes (rectangle, ramp-down triangle, ramp-up triangle) at different pulse widths and pulse frequencies have on detected amplitudes of electromyographs.
Figure 11B:
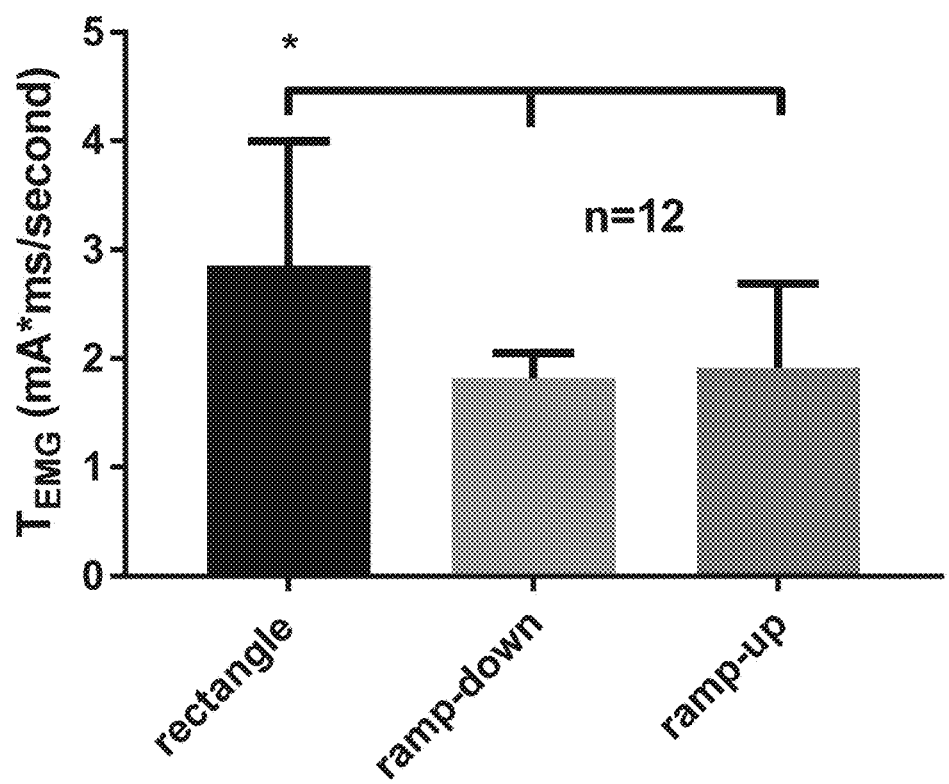
Figure 11C:
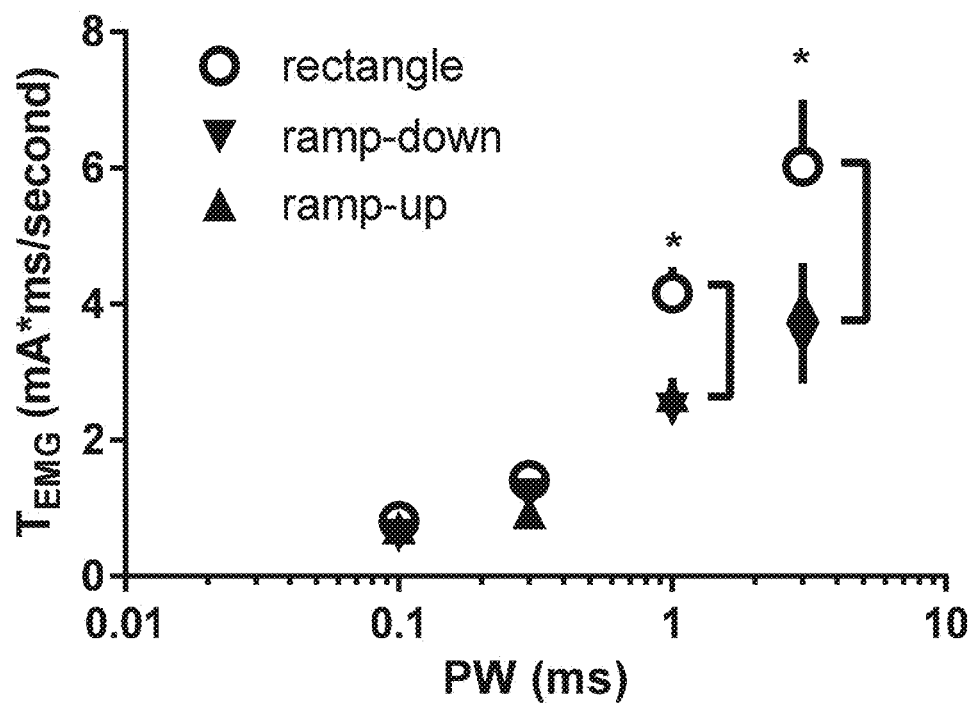
Figure 11D:
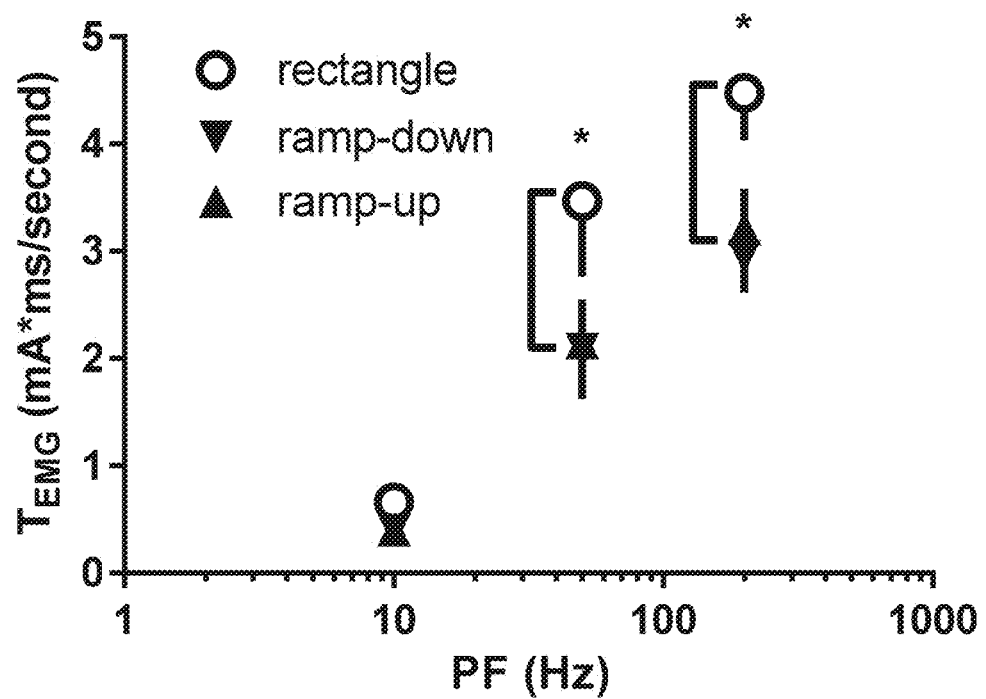

FIGS. 11A-D provide graphs related to the mixed model analysis of relationships among different parameters of SCS to trigger $T_{EMG}$s, including data of $T_{EMG}$ to different waveform shapes (rectangle, ramp-down triangle, ramp-up triangle as some examples) of SCS with different pulse widths and pulse frequencies. $T_{EMG}$s of SCS are expressed using pulse amplitude at mA (FIG. 11A) or current charge per second (mA*ms/second), which are calculated by (pulse amplitude)*(pulse width)*(pulse frequency) as shown in FIG. 11B. There are correlations of current charges between waveform shapes and pulse width as shown in FIG. 11C or between waveform shapes and pulse frequency (*, p<0.05, ANOVA Bonferroni post test) as shown in FIG. 11D.

Compared to an intra-pulse interval of 0 ms (e.g., no intra-pulse interval), introduction of a 0.1 ms or 0.3 ms intra-pulse interval tended to decrease the EMG response thresholds (mixed model, p=0.0536). The EMG response thresholds to SCS were waveform shape dependent (p<0.0001). As shown in FIG. 11A, at all pulse widths, pulse frequencies, and intra-pulse intervals tested, the rectangle waveform had the lowest threshold to trigger EMG responses. In other words, a rectangle shape pulse achieves the threshold at the lowest EMG amplitude, while the ramp-up pulse shape results in the highest threshold amplitude. However, the stimulation charge ((pulse amplitude)*(pulse width)) per second) was higher with the rectangular pulse shape than the charge intensities associated with ramp-down or ramp-up triangle stimulation (p<0.0001, FIG. 11B). In other words, the larger charge provided by the rectangular pulses result in lower stimulation thresholds for the subject.

Finally, mixed model analysis of SCS charges demonstrated correlations of waveform shapes with pulse width (FIG. 11C) and pulse frequency (FIG. 11D). The charge per second was significantly higher for rectangle pulse shapes when the pulse width was equal to or higher than 1 ms and pulse frequency that is higher than 50 Hz. In this manner, pulse shapes may be varied at higher pulse widths and pulse frequencies to augment charge delivered to the subject.

The recorded EMGs are physiological responses to SCS since they increase when stimulus intensities increase and disappear when rats are euthanized. The pulse frequency dependency of EMG response in rats may be similar to human studies showing that perception thresholds are inversely proportional to the SCS frequency. Data from the preclinical work suggest that there are several principles of motor responses to different parameters of electrode stimulation on the spinal cord, which may be referenced to expedite charge delivery of SCS in preclinical tests or clinical practice. Comparing EMG response thresholds expressed in charge per second with different pulse frequency and pulse width, there is higher charge delivery required to evoke an EMG response when stimulating with higher pulse frequencies/pulse widths versus lower pulse frequencies/pulse widths. Therefore, there may be three charge levels, of increasing charge intensities, to trigger EMG responses, such as (1) 10 Hz-1 kHz and 0.03 ms pulse width <(2) 10 Hz-1 kHz, 0.24 ms pulse width <(3) 1-10 kHz, 0.03 ms pulse width. The stimulation charge ((pulse amplitude)*(pulse width) per second) of rectangular waveform is higher than that associated with ramp-down or ramp-up triangle stimulation, especially when the pulse width is higher than 1 ms and pulse frequency is higher than 50 Hz. In this manner, the pulse waveform may be adjusted to achieve desired charge levels and thresholds, such as one or more of perception thresholds, discomfort thresholds, and/or motor thresholds.

In clinical practice, the stimulation intensity can be set at a maximal possible value, e.g., 60% or 80% sensory (or perception) threshold. Other parameters such as pulse width (or waveform shapes) can be effective parameters per pulse when defining the stimulation intensity. The EMG response thresholds (mA) decreased when pulse width increased or pulse amplitude (PA) is set at constant (rectangle). Charge delivery to the spinal cord is multiplying the pulse amplitude (PA) (in mA) by the pulse width as ∫Id(t). The strength-duration curve demonstrates that wider pulse widths or rectangle waveform stimulations require lower amplitudes, but higher charges to evoke the EMG responses.

Energy consumption and therapy outcomes are two different issues of the stimulation therapy. Traditionally the time constant (chronaxie, proportional to time constant) of pulse width dependent nerve activation (strength-duration curve) has been used to characterize the membrane and morphological properties of the stimulated tissue and may represent a desired or target pulse width regarding the charge delivery into the tissue. This is still true especially when chronaxie is used to estimate properties changes of the nervous system, composition of activated nerve fibers, thickness of the cerebrospinal fluid layer, which is assumed to be the distance between the stimulating electrode and the epidural space of the spinal cord, spinal cord movement and others.

However, chronaxie may not relate to patient-preferred stimulation settings. The insufficient coverage or coverage loss is a common problem in clinic, as wider pulse widths result in greater pain-paresthesia coverage and comfort for patient. For instance, the coverage can increase 61.75% when the pulse width increases from 0.05 ms to 0.5 ms and it stays practically stable between 0.5 ms and 1 ms. A range of optimal pulse widths have been reported, e.g., 0.45 ms-0.5 ms, 1.5 ms, or up to 0.7 ms, but patients can be dissatisfied at pulse widths of 0.75 ms.

As the duration of the stimulus (i.e., pulse width) increases, an increase in the recruitment of nerve fibers occurs, which widens the stimulation area and improves the therapeutic range. Since there is a greater relative fraction of smaller fibers in the medial aspects of the dorsal columns, therefore, there is greater paresthesia coverage in the lumbar and sacral dermatomes with increased pulse width at a mid- to low-thoracic lead placement.

The pulse widths, which are potentially more effective at relieving pain, that are wider than chronaxie may be more effective. Therefore, the classic pulse width values obtained in the chronaxie-rheobase curve may be used for estimating lead location and characterizing nerve properties related to the spinal cord stimulation on pain relief, but they are not adequate for the usual programming of therapy. Pulse width selection may depend on both stimulation coverage of the painful area by the paresthesia and stimulation quality perceived by the patient.

The criteria of pulse width selection may vary among different mechanisms of stimulation therapies. Shorter pulse width of sacral neuromodulation may be more effective than longer pulse width. Pulse width affects the relative selectivity of stimulation among different types of nerve fibers. Thus, preferential activation of large nerve fibers over small fibers can be more pronounced with a shorter pulse width stimulation. This may be more effective than sacral neuromodulation on bladder functions since activations of fast conducting fibers, but not C-fiber afferents, can be needed for peripheral neuromodulation action. This has been supported by preclinical work that neuromodulation produces a stronger inhibition on bladder activities when the primary afferent C-fibers are desensitized by chronic pretreatment with a high dose of capsaicin in rats. Activation of C-fibers may stimulate bladder afferent activity (urgency), and consequently weaken the inhibitory effect of neuromodulation. The intensity window of sacral neuromodulation between activating maximally on fast conducting fibers and minimally on small C fibers may be small. Therefore, shorter pulse width stimulation may increase the window and reduce discomfort due to higher nerve fiber selectivity compared to the 0.21 ms PW that is widely used clinically. Meanwhile, shorter PW neuromodulation may be advantageous due to potential decrease in battery-referred current consumption which subsequently, can enhance device longevity or battery recharge intervals.

According to the above data, when the pulse frequency was less than 100 Hz, each EMG waveform is coupled to each stimulus while the latency is about 3 ms-4 ms. This frequency range is used often in clinical practice (e.g., 40 Hz-100 Hz). At low frequency, the paresthesia can be perceived as pounding while higher frequencies can lead to a tingling sensation or paresthesia-free. In contrast to what occurs during pulse width variation, changes in pulse frequency do not appear to influence significantly the paresthesia coverage (80% of the area for 40 Hz vs. 94% of the area for 1200 Hz). At pulse frequencies less than 100 Hz, theoretically each pulse above the activation threshold is able to evoke one set of action potentials, and continuous pulses may fire neurons in a synchronous manner. The strength-duration curve would accurately demonstrate characteristic of neural activation at the spinal cord. Threshold in charge will be approximately proportional to the product of pulse amplitude, pulse width, and pulse frequency.

As the pulse amplitude, pulse width, and pulse frequency increased, charge increased, and the latency decreased up to saturation. Therefore, the latency of EMG to SCS is correlated with charge (per second). There were clear separations of response curves, which yielded three possible charge levels of increasing intensities to trigger EMG responses: 200 Hz-1 kHz and 0.03 ms pulse width <200 Hz-1 kHz and 0.24 ms pulse width <5 kHz-10 kHz and 0.03 ms pulse width. Pulse frequencies greater than 1 kHz-10 kHz deliver the highest charges while pulse frequencies less than 1 kHz at a 0.03 ms pulse width stimulations generate the lowest charges in the tested parameter values discussed above.

The three charge zones of SCS identified by the examples above could be explained by a hypothesis of "pseudo-random" or stochastic neuron activation to high frequency SCS. There is evidence that neuron activation is able to couple to stimulation at rates less than 200 Hz and could entrain electrical stimulation around 200 Hz-900 Hz. Different neurons have different excitability, so exact charge to generate an action potential differs for each neuron. As the pulse frequency increases, more neurons will generate action potentials and result in obtaining larger coverage areas at lower thresholds. As the rate was increased to the kilohertz range, clusters of fibers initially responded synchronously but, by the tenth stimulus, neurons began to "drop out" as demonstrated by lower compound action potential amplitudes. This "drop out" phenomenon may be caused by "refractory period" from each neuron where the neuron is not being capable of reacting to another stimulating pulse for a couple of milliseconds. The refractory period is related inversely to the diameter of the neuron. Increasing frequencies will recruit smaller diameter fibers and a greater therapeutic effect may be achieved. Indeed, more "energy" would be "wasted" on "drop out" to super-high frequency of SCS. Therefore, stimulation parameter values may be selected to reduce stimulation during this "drop out" period of no evoked potentials to reduce power consumption by the device.

The charge per second is calculated by determining the charge delivered in 1 second of time. This concept of the charge delivery over time has been recently described. The results suggest that higher charge delivery could be accomplished by increasing pulse amplitude, pulse width, and pulse frequency and rectangle waveform shape. The significant highest charge is associated with pulse frequencies of greater than approximately 1 kHz.

Once again, energy consumption and therapy outcomes may be two different targets for the clinician and the patient, and these targets may or may not converge. High pulse frequency stimulation may achieve pain relief, and 10 kHz can provide better analgesia than other methods of stimulation in some examples. However, it is not clear whether 10 kHz is the best high frequency for SCS analgesia, or if other frequencies may provide a better balance between energy consumption and therapy outcome. In some cases, 1 kHz and 10 kHz can be equally effective in attenuation of hypersensitivity in SNL rats or rats with nerve lesion. Level 1 evidence suggests an equivalent pain relief and improvements in quality of life from 1 kHz to 10 kHz SCS. If 1 kHz provides the same therapeutic benefits compared to higher frequencies, using less charge can be expected to be beneficial for patients while consuming less energy.

Burst stimulation may offer a novel stimulation modality to attenuate pain without uncomfortable paresthesia. The number of pulses at one burst has arbitrarily been chosen. From the latency of EMG response in this study, it could be estimated the number of pulses required to evoke the EMG response. In the case of FIG. 10A, for example, two pulses at 0.2 mA of 200 Hz (intra-pulse frequency for bursts) are able to trigger EMG responses, but only one pulse at 0.6 mA is strong enough to produce nerve activation. The latency-stimulation intensity relationship could provide guidance to design a burst waveform, though other parameters, e.g., inter-pulse frequency can be considered.

Objective EMG response, but not sensory behavior to SCS, was used as markers of SCS in rats. Capturing the EMG response to SCS is a reasonable biomarker to SCS since motor responses are success markers of lead placement in clinical practice. In addition, intraoperative EMG testing can predict post-operative stimulation intensity. The EMG response threshold differs from perception threshold to SCS in rodents or human. Such proportional differences between motor threshold and perception threshold may not matter if both motor response threshold and sensory threshold correlate to each other. Although EMG is described, ECAP values may be measured in other examples.

However, EMG threshold in rats may or may not be comparable with the paresthesia threshold in humans. When analyzing the data on EMG response thresholds, the largest changes in the currents with pulse frequency are in the pulse frequency range of 10 Hz-1 kHz. This is consistent with clinical findings that higher frequencies are inversely proportional to perception threshold and the largest change occurring around 750 Hz. The similarity of pulse frequency dependent threshold response between EMG response in rats compared with the sensation threshold in human indicates that EMG response may be a reasonable biomarker representing the clinical responses to SCS.

Since an uncomfortable sensation can be triggered when the stimulation intensity is higher than response threshold, the results herein provide strategies to manipulate other parameter values (e.g., higher pulse width and pulse frequency) under the strength duration curves (e.g., below perceptible sensation) to deliver larger amounts of charge to the spinal cord. Higher charge delivery could be accomplished by increasing amplitude, wider pulse widths and/or higher frequency. Another way is to change the waveform shapes depending on pulse width and pulse frequency. For example, rectangle waveform can provide higher charge per second than triangle waveforms when pulse widths are greater than 1 ms or pulse frequency is greater than 30 Hz. Instead of increasing one parameter value, e.g., intensity with potential production of an uncomfortable sensation, these strategies use the extremes of pulse width, pulse frequency, or waveform shapes to deliver large amounts of charge to the spinal cord without discomfort or even a perceptible sensation. These results provide multiple strategies to manipulate parameters under the strength duration curves (e.g., below perceptible sensation) to deliver larger amounts of charge to the spinal cord.

The following examples are intended to illustrate various techniques, devices, and systems described herein.

Example 1: A system comprising a memory configured to store a relationship between a plurality of stimulation parameters, wherein values of the plurality of stimulation parameters are selectable to at least partially define electrical stimulation deliverable to a patient; and processing circuitry configured to: control a medical device to deliver a first electrical stimulation according to a first value of a first stimulation parameter of the plurality of stimulation parameters and a first value of a second parameter of the plurality of stimulation parameters; receive an input representative of an efficacy of the first electrical stimulation delivered to the patient according to the first value of the first stimulation parameter and the first value of the second parameter; select, based on the input and the relationship between the plurality of stimulation parameters, a second value of at least one of the first stimulation parameter or the second stimulation parameter; and control the medical device to deliver a second electrical stimulation according to the second value of the at least one of the first stimulation parameter or the second stimulation parameter.

Example 2: The system of example 1, further comprising a stimulation generator configured to generate the first electrical stimulation and the second electrical stimulation; and one or more electrodes configured to deliver the first electrical stimulation and the second electrical stimulation generated by the stimulation generator.

Example 3: The system of any of examples 1 or 2, wherein the medical device is an implantable medical device comprising a stimulation generator.

Example 4: The system of any of examples 1 through 3, wherein at least one of the medical device or an external programmer in communication with the medical device comprises the processing circuitry.

Example 5: The system of any of examples 1 through 4, further comprising a user interface configured to receive the input representative of the efficacy.

Example 6: The system of any of examples 1 through 5, wherein the plurality of stimulation parameters comprises at least two of: a pulse frequency, a pulse width, an amplitude, an intra-pulse interval, a duty cycle, a charge per second, or a waveform shape.

Example 7: The system of any of examples 1 through 6, wherein the stored relationship defines changes to respective values of at least one stimulation parameter of the plurality of stimulation parameters between a first zone, a second zone, and a third zone of stimulation intensity, wherein: the first zone comprises a pulse frequency range between approximately 10 hertz (Hz) and approximately 1 kilohertz (kHz) and a pulse width range between approximately 0.01 millisecond (ms) and approximately 0.1 ms; the second zone comprises a pulse frequency range between approximately 10 Hz and approximately 1 kHz and a pulse width range between approximately 0.1 ms and approximately 1.0 ms; and the third zone comprises a pulse frequency range between approximately 5 kHz and approximately 10 kHz and a pulse width range between approximately 0.01 ms and approximately 0.1 ms.

Example 8: The system of example 7, wherein the processing circuitry is configured to select the second value of at least one of the first stimulation parameter or the second stimulation parameter to be within the second zone in response to the efficacy of the first electrical stimulation being insufficient.

Example 9: The system of example 7, wherein the processing circuitry is configured to select the second value from at least one of the second zone or the third zone based on the stimulation parameter values selected for the first zone.

Example 10: The system of example 7, wherein the processing circuitry is configured to select stimulation parameter values configured to define electrical stimulation providing increasing levels of charge between each zone.

Example 11: The system of example 7, wherein the first zone comprises the pulse width of approximately 0.03 millisecond (ms), the second zone comprises the pulse width of approximately 0.24 ms, and the third zone comprises the pulse width of approximately 0.03 ms.

Example 12: The system of any of examples 1 through 11, wherein the processing circuitry is configured to determine a relationship between a received electrical compound action potential (ECAP) signal and the plurality of stimulation parameters, and wherein the processing circuitry is configured to select the second value of at least one of the first stimulation parameter or the second stimulation parameter based upon on the relationship between the received ECAP signal and the plurality of stimulation parameters.

Example 13: The system of example 12, wherein the plurality of stimulation parameters comprises a pulse frequency, and wherein the processing circuitry is configured to select, based on the relationship, the second value as a second pulse frequency for the second electrical stimulation that is higher than a first pulse frequency of the first electrical stimulation.

Example 14: The system of any of examples 1 through 13, wherein the processing circuitry is configured to select stimulation parameters below a strength-duration curve.

Example 15: The system of any of examples 1 through 14, wherein the processing circuitry is configured to select the second value of at least one of the first stimulation parameter or the second stimulation parameter according to the stored relationship and according to charge associated with values of at least one of the first stimulation parameter or the second stimulation parameter to reduce power consumption.

Example 16: The system of any of examples 1 through 15, wherein the processing circuitry is configured to maintain stimulation intensity between the first electrical stimulation and the second electrical stimulation.

Example 17: A method comprising storing, in memory, a relationship between a plurality of stimulation parameters, wherein values of the plurality of stimulation parameters are selectable to at least partially define electrical stimulation deliverable to a patient; controlling, by processing circuitry, a medical device to deliver a first electrical stimulation according to a first value of a first stimulation parameter of the plurality of stimulation parameters and a first value of a second parameter of the plurality of stimulation parameters; receiving, by the processing circuitry, an input representative of an efficacy of the first electrical stimulation delivered to the patient according to the first value of the first stimulation parameter and the first value of the second parameter; selecting, by the processing circuitry and based on the input and the relationship between the plurality of stimulation parameters, a second value of at least one of the first stimulation parameter or the second stimulation parameter; and controlling, by the processing circuitry, the medical device to deliver a second electrical stimulation according to the second value of the at least one of the first stimulation parameter or the second stimulation parameter.

Example 18: The method of example 17, further comprising a stimulation generator configured to generate the first electrical stimulation and the second electrical stimulation; and one or more electrodes configured to deliver the first electrical stimulation and the second electrical stimulation generated by the stimulation generator.

Example 19: The method of any of examples 17 and 18, the medical device is an implantable medical device comprising a stimulation generator.

Example 20: The method of any of examples 17 through 19, wherein at least one of the medical device or an external programmer in communication with the medical device comprises the processing circuitry.

Example 21: The method of any of examples 17 through 20, further comprising receiving, by a user interface, the input representative of the efficacy.

Example 22: The method of any of examples 17 through 21, wherein the plurality of stimulation parameters comprises at least two of: a pulse frequency, a pulse width, an amplitude, an intra-pulse interval, a duty cycle, a charge per second, or a waveform shape.

Example 23: The method of any of examples 17 through 22, wherein the stored relationship defines changes to respective values of at least one stimulation parameter of the plurality of stimulation parameters between a first zone, a second zone, and a third zone of stimulation intensity, wherein: the first zone comprises a pulse frequency range between approximately 10 hertz (Hz) and approximately 1 kilohertz (kHz) and a pulse width range between approximately 0.01 millisecond (ms) and approximately 0.1 ms; the second zone comprises a pulse frequency range between approximately 10 Hz and approximately 1 kHz and a pulse width range between approximately 0.1 ms and approximately 1.0 ms; and the third zone comprises a pulse frequency range between approximately 5 kHz and approximately 10 kHz and a pulse width range between approximately 0.01 ms and approximately 0.1 ms.

Example 24: The method of example 23, wherein selecting the second value comprises selecting the second value of at least one of the first stimulation parameter or the second stimulation parameter to be within the second zone in response to the efficacy of the first electrical stimulation being insufficient.

Example 25: The method of example 23, wherein selecting the second value comprises selecting the second value from at least one of the second zone or the third zone based on the stimulation parameter values selected for the first zone.

Example 26: The method of example 23, wherein selecting the second value or other values of at least the first stimulation parameter or the second stimulation parameter comprises selecting the second value or the other values of the at least the first stimulation parameter or the second stimulation parameter to define electrical stimulation providing increasing levels of charge between each zone.

Example 27: The method of example 23, wherein the first zone comprises the pulse width of approximately 0.03 millisecond (ms), the second zone comprises the pulse width of approximately 0.24 ms, and the third zone comprises the pulse width of approximately 0.03 ms.

Example 28: The method of any of examples 17 through 27, further comprising determining a relationship between a received electrical compound action potential (ECAP) signal and the plurality of stimulation parameters, and wherein selecting the second value comprises selecting the second value of at least one of the first stimulation parameter or the second stimulation parameter based upon on the relationship between the received ECAP signal and the plurality of stimulation parameters.

Example 29: The method of example 28, wherein the plurality of stimulation parameters comprises a pulse frequency, and wherein selecting the second value comprises selecting, based on the relationship, the second value as a second pulse frequency for the second electrical stimulation that is higher than a first pulse frequency of the first electrical stimulation.

Example 30: The method of any of examples 17 through 29, further comprising selecting stimulation parameters below a strength-duration curve.

Example 31: The method of any of examples 17 through 30, wherein selecting the second value comprises selecting the second value of at least one of the first stimulation parameter or the second stimulation parameter according to the stored relationship and according to charge associated with values of at least one of the first stimulation parameter or the second stimulation parameter to reduce power consumption.

Example 32: The method of any of examples 17 through 31, further comprising maintaining stimulation intensity between the first electrical stimulation and the second electrical stimulation.

Example 33: A computer-readable storage medium comprising instructions that, when executed by processing circuitry of a medical device, cause the processing circuitry to: receive a relationship between a plurality of stimulation parameters, wherein values of the plurality of stimulation parameters are selectable to at least partially define electrical stimulation deliverable to a patient; control a medical device to deliver a first electrical stimulation according to a first value of a first stimulation parameter of the plurality of stimulation parameters and a first value of a second parameter of the plurality of stimulation parameters; receive an input representative of an efficacy of the first electrical stimulation delivered to the patient according to the first value of the first stimulation parameter and the first value of the second parameter; select, based on the input and a relationship between the plurality of stimulation parameters, a second value of at least one of the first stimulation parameter or the second stimulation parameter; and control the medical device to deliver a second electrical stimulation according to the second value of the at least one of the first stimulation parameter or the second stimulation parameter.

Example 34: A system comprising a memory configured to store a relationship between a plurality of stimulation parameters, the plurality of stimulation parameters comprising a pulse frequency and a pulse width; and processing circuitry configured to: receive a signal representative of an evoked compound action potential (ECAP) elicited from electrical stimulation; determine, from the signal, a value of the ECAP indicative of a target stimulation intensity at least partially caused by a first set of stimulation parameter values comprising a first value of the pulse frequency and a first value of the pulse width of the electrical stimulation; determine, based on the relationship and the value of the ECAP, a second set of stimulation parameter values comprising at least one of a second value of the pulse frequency greater than the first value of the pulse frequency or a second value of the pulse width greater than the first value of the pulse width; and control a medical device to deliver electrical stimulation according to the second set of stimulation parameter values.

Example 35: The system of example 34, further comprising a stimulation generator configured to deliver the electrical stimulation according to the second set of stimulation parameters.

Example 36: The method of any of examples 34 and 35, wherein the processing circuitry is configured to determine the second set of stimulation parameter values by selecting at least the second value of the pulse frequency or the second value of the pulse width from values under a strength-duration curve representing relationships between at least one of amplitude and pulse frequency or amplitude and pulse width indicative of the target stimulation intensity.

Example 37: The method of any of examples 34 through 36, wherein the processing circuitry is configured to determine the relationship between the plurality of stimulation parameters by determining the relationship between the value of the ECAP indicative of the target stimulation intensity and the plurality of stimulation parameters.

Example 38: The method of any of examples 34 through 37, wherein the processing circuitry is configured to determine the second set of stimulation parameter values by selecting the second value of the pulse frequency to be greater than the first value of the pulse frequency and the second value of the pulse width to be greater than the first value of the pulse width.

Example 39: A method comprising storing a relationship between a plurality of stimulation parameters, the plurality of stimulation parameters comprising a pulse frequency and a pulse width; receiving a signal representative of an evoked compound action potential (ECAP) elicited from electrical stimulation; determining, from the signal, a value of the ECAP indicative of a target stimulation intensity at least partially caused by a first set of stimulation parameter values comprising a first value of the pulse frequency and a first value of the pulse width of the electrical stimulation; determining, based on the relationship and the value of the ECAP, a second set of stimulation parameter values comprising at least one of a second value of the pulse frequency greater than the first value of the pulse frequency or a second value of the pulse width greater than the first value of the pulse width; and controlling a medical device to deliver electrical stimulation according to the second set of stimulation parameter values.

Example 40: The method of example 39, further comprising delivering the electrical stimulation according to the second set of stimulation parameters.

Example 41: The method of any of examples 39 and 40, wherein determining the second set of stimulation parameter values comprises selecting at least the second value of the pulse frequency or the second value of the pulse width from values under a strength-duration curve representing relationships between at least one of amplitude and pulse frequency or amplitude and pulse width indicative of the target stimulation intensity.

Example 42: The method of any of examples 39 through 41, wherein determining the relationship between the plurality of stimulation parameters comprises determining the relationship between the value of the ECAP indicative of the target stimulation intensity and the plurality of stimulation parameters.

Example 43: The method of any of examples 39 through 42, wherein determining the second set of stimulation parameter values comprises selecting the second value of the pulse frequency to be greater than the first value of the pulse frequency and the second value of the pulse width to be greater than the first value of the pulse width.

Example 44: A system comprises a memory configured to store a relationship between a plurality of stimulation parameters, wherein values of the plurality of stimulation parameters are selectable to at least partially define electrical stimulation deliverable to a patient; and processing circuitry configured to: control a medical device to deliver a first electrical stimulation within a first zone of a plurality of intensity zones to a patient, wherein the first zone comprises a first pulse frequency range and a first pulse width range; determine that the first electrical stimulation provides ineffective therapy for the patient; select, based on the first electrical stimulation providing ineffective therapy for the patient, a second pulse frequency value from a second pulse frequency range of a second zone of the plurality of intensity zones and a second pulse width value from a second pulse width range of the second zone, wherein at least one of the second pulse frequency range is greater than the first pulse frequency range or the second pulse width range is greater than the first pulse width range, and wherein stimulation parameter values selected from the second zone define a second electrical stimulation having a second stimulation intensity greater than a first stimulation intensity of the first electrical stimulation; and control the medical device to deliver the second electrical stimulation to the patient.

Example 45: The system of example 44, wherein the processing circuitry is configured to: select, in response to determining that the second electrical stimulation provides ineffective therapy for the patient, a third pulse frequency value from a third pulse frequency range of a third zone of the plurality of intensity zones and a third pulse width value from a third pulse width range of the third zone, wherein at least one of the third pulse frequency range is greater than the second pulse frequency range or the third pulse width range is less than the second pulse width range, and wherein stimulation parameter values selected from the third zone define a third electrical stimulation having a third stimulation intensity greater than the second stimulation intensity of the second electrical stimulation, and control delivery of the third electrical stimulation to the patient.

Example 46: The system of any of examples 44 and 45, wherein the third zone defines a third pulse frequency range of between approximately 5 kilohertz (kHz) and approximately 10 kHz and a third pulse width range of between approximately 0.01 millisecond (ms) and approximately 0.1 ms.

Example 47: The system of any of examples 44 through 46, wherein the first zone defines the first pulse frequency range of between approximately 10 hertz (Hz) and approximately 1 kilohertz (kHz) and the first pulse width range between approximately 0.01 millisecond (ms) and approximately 0.1 ms, and the second zone defines the second pulse frequency range of between approximately 10 Hz and approximately 1 kHz and the second width range of between approximately 0.1 ms and approximately 1.0 ms.

Example 48: The system of any of examples 44 through 47, wherein the processing circuitry is configured to store, in the memory, relationships between the stimulation parameter values selected from the first zone and second zone, wherein the stored relationships define how to change values of stimulation parameters when changing between the first zone and the second zone.

Example 49: A method comprising storing a relationship between a plurality of stimulation parameters, wherein values of the plurality of stimulation parameters are selectable to at least partially define electrical stimulation deliverable to a patient; controlling, by processing circuitry, delivery of a first electrical stimulation within a first zone of a plurality of intensity zones to a patient, wherein the first zone comprises a first pulse frequency range and a first pulse width range; determining, by the processing circuitry, that the first electrical stimulation provides ineffective therapy for the patient; responsive to determining that the first electrical stimulation provides ineffective therapy for the patient, selecting, by the processing circuitry, a second pulse frequency value from a second pulse frequency range of a second zone of the plurality of intensity zones and a second pulse width value from a second pulse width range of the second zone, wherein at least one of the second pulse frequency range is greater than the first pulse frequency range or the second pulse width range is greater than the first pulse width range, and wherein stimulation parameter values selected from the second zone define a second electrical stimulation having a second stimulation intensity greater than a first stimulation intensity of the first electrical stimulation; and controlling, by the processing circuitry, delivery of the second electrical stimulation to the patient.

Example 50: The method of example 49, wherein, responsive to determining that the second electrical stimulation provides ineffective therapy for the patient, further comprising: selecting a third pulse frequency value from a third pulse frequency range of a third zone of the plurality of intensity zones and a third pulse width value from a third pulse width range of the third zone, wherein at least one of the third pulse frequency range is greater than the second pulse frequency range or the third pulse width range is less than the second pulse width range, and wherein stimulation parameter values selected from the third zone define a third electrical stimulation having a third stimulation intensity greater than the second stimulation intensity of the second electrical stimulation; and controlling delivery of the third electrical stimulation to the patient.

Example 51: The method of example 50, wherein the third zone defines a third pulse frequency range of between approximately 5 kilohertz (kHz) and approximately 10 kHz and a third pulse width range of between approximately 0.01 millisecond (ms) and approximately 0.1 ms.

Example 52: The method of any of examples 49 through 51, wherein the first zone defines the first pulse frequency range of between approximately 10 hertz (Hz) and approximately 1 kilohertz (kHz) and the first pulse width range between approximately 0.01 millisecond (ms) and approximately 0.1 ms, and the second zone defines the second pulse frequency range of between approximately 10 Hz and approximately 1 kHz and the second width range of between approximately 0.1 ms and approximately 1.0 ms.

Example 53: The method of any of examples 49 through 52, further comprising storing relationships between the stimulation parameter values selected from the first zone and second zone, wherein the stored relationships define how to change values of stimulation parameters when changing between the first zone and the second zone.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A system comprising:
a memory configured to store a plurality of zones, each zone of the plurality of zones defining a range of values for one or more stimulation parameters that at least partially define electrical stimulation deliverable to a patient; and
processing circuitry configured to:
control a medical device to deliver a first electrical stimulation according to a first zone of the plurality of zones that defines a first range of values for a first stimulation parameter of the one or more stimulation parameters;
receive an input representative of an efficacy of the first electrical stimulation delivered to the patient according to the first zone;
determine that efficacy of the first electrical stimulation is insufficient based on the input representative of the efficacy;
responsive to determining that the efficacy of the first electrical stimulation is insufficient, select a second zone of the plurality of zones that define a second range of values for the first stimulation parameter, the second range being different than the first range; and
control the medical device to deliver a second electrical stimulation according to the second zone that defines the second range of values for the first stimulation parameter.

2. The system of claim 1, wherein the first zone defines a third range of values for a second stimulation parameter of the plurality of stimulation parameters, and wherein the second zone defines a fourth range of values for the second stimulation parameter, the third range being different than the fourth range.

3. The system of claim 1, wherein the input is a first input, and wherein the efficacy is a first efficacy, and wherein the processing circuitry is further configured to:
   receive a second input representative of a second efficacy of the second electrical stimulation delivered to the patient according to the second zone;
   determine that second efficacy of the second electrical stimulation is insufficient based on the second input representative of the second efficacy;
   responsive to determining that the second efficacy of the second electrical stimulation is insufficient, select a third zone of the plurality of zones that define a third range of values for the first stimulation parameter, the third range being different than the first range and the second range; and
   control the medical device to deliver a third electrical stimulation according to the third zone that defines the third range of values for the first stimulation parameter.

4. The system of claim 1, wherein:
   the input is a first input and the efficacy is a first efficacy,
   the first zone defines the first range of values for the first stimulation parameter and a third range of values for a second stimulation parameter,
   the second zone defines the second range of values for the first stimulation parameter and the third range of values for the second stimulation parameter, and
   the processing circuitry is further configured to:
      receive a second input representative of a second efficacy of the second electrical stimulation delivered to the patient according to the second zone;
      determine that second efficacy of the second electrical stimulation is insufficient based on the second input representative of the second efficacy; and
      responsive to determining that a second efficacy of the second electrical stimulation is insufficient, select a third zone of the plurality of zones that define the first range of values for the first stimulation parameter and a fourth range of values for the second stimulation parameter for third electrical stimulation.

5. The system of claim 4, wherein:
   the first zone comprises a pulse frequency range as the third range between approximately 10 hertz (Hz) and approximately 1 kilohertz (kHz) and a pulse width range as the first range between approximately 0.01 millisecond (ms) and approximately 0.1 ms;
   the second zone comprises a pulse frequency range as the third range between approximately 10 Hz and approximately 1 kHz and a pulse width range as the second range between approximately 0.1 ms and approximately 1.0 ms; and
   the third zone comprises a pulse frequency range as the fourth range between approximately 5 kHz and approximately 10 kHz and a pulse width range as the first between approximately 0.01 ms and approximately 0.1 ms.

6. The system of claim 4, wherein the processing circuitry is configured to select stimulation parameter values configured to define electrical stimulation providing increasing levels of charge between each zone.

7. The system of claim 4, wherein:
   the first zone comprises the pulse width of approximately 0.03 millisecond (ms),
   the second zone comprises the pulse width of approximately 0.24 ms, and
   the third zone comprises the pulse width of approximately 0.03 ms.

8. The system of claim 1, wherein the second electrical stimulation according to the second zone has a greater intensity of stimulation than the first electrical stimulation according to the first zone.

9. The system of claim 1, wherein the plurality of stimulation parameters comprises at least two of: a pulse frequency, a pulse width, an amplitude, an intra-pulse interval, a duty cycle, a charge per second, or a waveform shape.

10. The system of claim 1, wherein the processing circuitry is configured to determine a relationship between a received electrical compound action potential (ECAP) signal and the plurality of stimulation parameters, and wherein the processing circuitry is configured to select a value within the second range of values for the first stimulation parameter based upon on the relationship between the received ECAP signal and the plurality of stimulation parameters.

11. The system of claim 1, further comprising:
   a stimulation generator configured to generate the first electrical stimulation and the second electrical stimulation; and
   one or more electrodes configured to deliver the first electrical stimulation and the second electrical stimulation generated by the stimulation generator.

12. The system of claim 1, further comprising a user interface configured to receive the input representative of the efficacy.

13. A method comprising:
   storing, in a memory, a plurality of zones, each zone of the plurality of zones defining a range of values for one or more stimulation parameters that at least partially defines electrical stimulation deliverable to a patient;
   controlling, by processing circuitry, a medical device to deliver a first electrical stimulation according to a first zone of the plurality of zones that defines a first range of values for a first stimulation parameter of the one or more stimulation parameters;
   receiving, by the processing circuitry, an input representative of an efficacy of the first electrical stimulation delivered to the patient according to the first zone;
   determining, by the processing circuitry, that efficacy of the first electrical stimulation is insufficient based on the input representative of the efficacy;
   responsive to determining that the efficacy of the first electrical stimulation is insufficient, selecting, by the processing circuitry, a second zone of the plurality of zones that define a second range of values for the first stimulation parameter, the second range being different than the first range; and
   controlling, by the processing circuitry, the medical device to deliver a second electrical stimulation according to the second zone that defines the second range of values for the first stimulation parameter.

14. The method of claim 13, wherein the first zone defines a third range of values for a second stimulation parameter of the plurality of stimulation parameters, and wherein the second zone defines a fourth range of values for the second stimulation parameter, the third range being different than the fourth range.

15. The method of claim 13, wherein the input is a first input, and wherein the efficacy is a first efficacy, and wherein the method further comprises:

receiving a second input representative of a second efficacy of the second electrical stimulation delivered to the patient according to the second zone;

determining that second efficacy of the second electrical stimulation is insufficient based on the second input representative of the second efficacy;

responsive to determining that the second efficacy of the second electrical stimulation is insufficient, selecting a third zone of the plurality of zones that define a third range of values for the first stimulation parameter, the third range being different than the first range and the second range; and controlling the medical device to deliver a third electrical stimulation according to the third zone that defines the third range of values for the first stimulation parameter.

16. The method of claim 13, wherein:

the input is a first input and the efficacy is a first efficacy, the first zone defines the first range of values for the first stimulation parameter and a third range of values for a second stimulation parameter, the second zone defines the second range of values for the first stimulation parameter and the third range of values for the second stimulation parameter, and the method further comprises:

receiving a second input representative of a second efficacy of the second electrical stimulation delivered to the patient according to the second zone;

determining that second efficacy of the second electrical stimulation is insufficient based on the second input representative of the second efficacy; and responsive to determining that a second efficacy of the second electrical stimulation is insufficient, selecting a third zone of the plurality of zones that define the first range of values for the first stimulation parameter and a fourth range of values for the second stimulation parameter for third electrical stimulation.

17. The method of claim 16, wherein:

the first zone comprises a pulse frequency range as the third range between approximately 10 hertz (Hz) and approximately 1 kilohertz (kHz) and a pulse width range as the first range between approximately 0.01 millisecond (ms) and approximately 0.1 ms;

the second zone comprises a pulse frequency range as the third range between approximately 10 Hz and approximately 1 kHz and a pulse width range as the second range between approximately 0.1 ms and approximately 1.0 ms; and the third zone comprises a pulse frequency range as the fourth range between approximately 5 kHz and approximately 10 kHz and a pulse width range as the first between approximately 0.01 ms and approximately 0.1 ms.

18. The method of claim 16, further comprising selecting stimulation parameter values configured to define electrical stimulation providing increasing levels of charge between each zone.

19. The method of claim 13, wherein the method further comprises determining a relationship between a received electrical compound action potential (ECAP) signal and the plurality of stimulation parameters, and wherein the processing circuitry is configured to select a value within the second range of values for the first stimulation parameter based upon on the relationship between the received ECAP signal and the plurality of stimulation parameters.

20. A computer-readable storage medium comprising instructions that, when executed, causes processing circuitry to:

store, in a memory, a plurality of zones, each zone of the plurality of zones defining a range of values for one or more stimulation parameters that at least partially defines electrical stimulation deliverable to a patient;

control a medical device to deliver a first electrical stimulation according to a first zone of the plurality of zones that defines a first range of values for a first stimulation parameter of the one or more stimulation parameters;

receive an input representative of an efficacy of the first electrical stimulation delivered to the patient according to the first zone;

determine that efficacy of the first electrical stimulation is insufficient based on the input representative of the efficacy;

responsive to determining that the efficacy of the first electrical stimulation is insufficient, select a second zone of the plurality of zones that define a second range of values for the first stimulation parameter, the second range being different than the first range; and control the medical device to deliver a second electrical stimulation according to the second zone that defines the second range of values for the first stimulation parameter.

* * * * *